US012752130B2

(12) United States Patent
Smith et al.
(10) Patent No.: US 12,752,130 B2
(45) Date of Patent: *Oct. 6, 2026

(54) TRIGGERED TREATMENT SYSTEMS AND METHODS

(71) Applicants: Varian Medical Systems, Inc., Palo Alto, CA (US); Siemens Healthineers International AG., Steinhausen (CH)

(72) Inventors: Christel Smith, Santa Barbara, CA (US); Corey Zankowski, San Jose, CA (US); Jan Hein Timmer, Los Altos, CA (US); Wolfgang Kaissl, Wil (CH); Deepak Khuntia, Los Altos, CA (US); Eric Abel, San Jose, CA (US); Josh Star-Lack, Palo Alto, CA (US); Camille Noel, St. Louis, MO (US)

(73) Assignees: VARIAN MEDICAL SYSTEMS, INC., Palo Alto, CA (US); SIEMENS HEALTHINEERS INTERNATIONAL AG, Steinhausen (CH)

( * ) Notice: Subject to any disclaimer, the term of this patent is extended or adjusted under 35 U.S.C. 154(b) by 219 days.

This patent is subject to a terminal disclaimer.

(21) Appl. No.: 18/637,764

(22) Filed: Apr. 17, 2024

(65) Prior Publication Data

US 2024/0278039 A1 Aug. 22, 2024

Related U.S. Application Data

(63) Continuation of application No. 17/132,966, filed on Dec. 23, 2020, now Pat. No. 11,986,677, which is a (Continued)

(51) Int. Cl.

| | |
|---|---|
| ***A61N 5/00*** | (2006.01) |
| ***A61N 5/10*** | (2006.01) |
| *A61B 90/00* | (2016.01) |

(52) U.S. Cl.

CPC ......... *A61N 5/1069* (2013.01); *A61N 5/1049* (2013.01); *A61N 5/1067* (2013.01); (Continued)

(58) Field of Classification Search

CPC ...... A61N 5/10; A61N 5/1069; A61N 5/1049; A61N 5/1067; A61N 5/1077; (Continued)

(56) References Cited

U.S. PATENT DOCUMENTS 4,163,901 A 8/1979 Azam et al.
4,914,681 A 4/1990 Klingenbeck et al.
(Continued)

FOREIGN PATENT DOCUMENTS

CN 101282760 A 10/2008
CN 104001270 A 8/2014
(Continued)

OTHER PUBLICATIONS

M. McManus et al., "The challenge of ionisation chamber dosimetry in ultra-short pulsed high dose-rate Very High Energy Electron beams," Sci Rep 10, 9089 (2020), published Jun. 3, 2020, https://doi.org/10.1038/s41598-020-65819-y.
(Continued)

*Primary Examiner* — Jurie Yun

(74) *Attorney, Agent, or Firm* — Harness, Dickey & Pierce, P.L.C.

(57) ABSTRACT

In various embodiments, a radiation therapy method can include loading a planning image of a target in a human. In addition, the position of the target can be monitored. A computation can be made of an occurrence of substantial alignment between the position of the target and the target of the planning image. Furthermore, after the computing, a beam of radiation is triggered to deliver a dosage to the target in a short period of time (e.g., less than a second).

20 Claims, 8 Drawing Sheets

Related U.S. Application Data continuation of application No. 16/237,502, filed on Dec. 31, 2018, now Pat. No. 10,898,730, which is a continuation of application No. 15/657,072, filed on Jul. 21, 2017, now Pat. No. 10,183,179.

(52) U.S. Cl.
CPC .... *A61N 5/1077* (2013.01); *A61B 2090/0481* (2016.02); *A61N 2005/1061* (2013.01); *A61N 2005/1094* (2013.01)

(58) Field of Classification Search
CPC .......... A61N 5/1075; A61N 2005/1061; A61N 2005/1094; A61B 2090/0481; A61B 90/00
See application file for complete search history.

(56) References Cited

U.S. PATENT DOCUMENTS 5,142,559 A 8/1992 Wielopolski et al.
5,153,900 A 10/1992 Nomikos et al.
5,267,294 A 11/1993 Kuroda et al.
5,550,378 A 8/1996 Skillicorn et al.
5,610,967 A 3/1997 Moorman et al.
5,625,663 A 4/1997 Swerdloff et al.
5,682,412 A 10/1997 Skillicorn et al.
5,757,885 A 5/1998 Yao et al.
6,198,802 B1 3/2001 Elliott et al.
6,222,544 B1 4/2001 Tarr et al.
6,234,671 B1 5/2001 Solomon et al.
6,260,005 B1 7/2001 Yang et al.
6,379,380 B1 4/2002 Satz
6,411,675 B1 6/2002 Llacer
6,445,766 B1 9/2002 Whitham
6,504,899 B2 1/2003 Pugachev et al.
6,580,940 B2 6/2003 Gutman
6,993,112 B2 1/2006 Hesse
7,268,358 B2 9/2007 Ma et al.
7,453,983 B2 11/2008 Schildkraut et al.
7,515,681 B2 4/2009 Ebstein
7,522,706 B2 4/2009 Lu et al.
7,560,715 B2 7/2009 Pedroni
7,590,219 B2 9/2009 Maurer, Jr. et al.
7,616,735 B2 11/2009 Maciunas et al.
7,623,623 B2 11/2009 Raanes et al.
7,778,691 B2 8/2010 Zhang et al.
7,807,982 B2 10/2010 Nishiuchi et al.
7,831,289 B2 11/2010 Riker et al.
7,835,492 B1 11/2010 Sahadevan
7,907,699 B2 3/2011 Long et al.
8,284,898 B2 10/2012 Ho et al.
8,306,184 B2 11/2012 Chang et al.
8,401,148 B2 3/2013 Lu et al.
8,406,844 B2 3/2013 Ruchala et al.
8,559,596 B2 10/2013 Thomson et al.
8,600,003 B2 12/2013 Zhou et al.
8,613,694 B2 12/2013 Walsh
8,636,636 B2 1/2014 Shukla et al.
8,644,571 B1 2/2014 Schulte et al.
8,716,663 B2 5/2014 Brusasco et al.
8,836,332 B2 9/2014 Shvartsman et al.
8,847,179 B2 9/2014 Fujitaka et al.
8,903,471 B2 12/2014 Heid
8,917,813 B2 12/2014 Maurer, Jr.
8,948,341 B2 2/2015 Beckman
8,958,864 B2 2/2015 Amies et al.
8,983,573 B2 3/2015 Carlone et al.
8,986,186 B2 3/2015 Zhang et al.
8,992,404 B2 3/2015 Graf et al.
8,995,608 B2 3/2015 Zhou et al.
9,018,603 B2 4/2015 Loo et al.
9,033,859 B2 5/2015 Fieres et al.
9,079,027 B2 7/2015 Agano et al.
9,149,656 B2 10/2015 Tanabe
9,155,908 B2 10/2015 Meltsner et al.
9,233,260 B2 1/2016 Slatkin et al.
9,258,876 B2 2/2016 Cheung et al.
9,283,406 B2 3/2016 Prieels
9,308,391 B2 4/2016 Liu et al.
9,330,879 B2 5/2016 Lewellen et al.
9,333,374 B2 5/2016 Iwata
9,468,777 B2 10/2016 Fallone et al.
9,517,358 B2 12/2016 Velthuis et al.
9,526,918 B2 12/2016 Kruip
9,545,444 B2 1/2017 Strober et al.
9,583,302 B2 2/2017 Figueroa Saavedra et al.
9,636,381 B2 5/2017 Basile
9,636,525 B1 5/2017 Sahadevan
9,649,298 B2 5/2017 Djonov et al.
9,656,098 B2 5/2017 Goer
9,694,204 B2 7/2017 Hårdemark
9,776,017 B2 10/2017 Flynn et al.
9,786,054 B2 10/2017 Taguchi et al.
9,786,093 B2 10/2017 Svensson
9,786,465 B2 10/2017 Li et al.
9,795,806 B2 10/2017 Matsuzaki et al.
9,801,594 B2 10/2017 Boyd et al.
9,844,358 B2 12/2017 Wiggers et al.
9,854,662 B2 12/2017 Mishin
9,884,206 B2 2/2018 Schulte et al.
9,931,522 B2 4/2018 Bharadwaj et al.
9,962,562 B2 5/2018 Fahrig et al.
9,974,977 B2 5/2018 Lachaine et al.
9,987,502 B1 6/2018 Gattiker et al.
10,007,961 B2 6/2018 Grudzinski et al.
10,022,564 B2 7/2018 Thieme et al.
10,071,264 B2 9/2018 Liger
10,080,912 B2 9/2018 Kwak et al.
10,092,774 B1 10/2018 Vanderstraten et al.
10,183,179 B1 * 1/2019 Smith .................. A61N 5/1069
10,188,875 B2 1/2019 Kwak et al.
10,206,871 B2 2/2019 Lin et al.
10,212,800 B2 2/2019 Agustsson et al.
10,232,193 B2 3/2019 Iseki
10,258,810 B2 4/2019 Zwart et al.
10,272,264 B2 4/2019 Ollila et al.
10,279,196 B2 5/2019 West et al.
10,293,184 B2 5/2019 Pishdad et al.
10,307,614 B2 6/2019 Schnarr
10,307,615 B2 6/2019 Ollila et al.
10,315,047 B2 6/2019 Glimelius et al.
10,413,755 B1 9/2019 Sahadevan
10,449,389 B2 10/2019 Ollila et al.
10,485,988 B2 11/2019 Kuusela et al.
10,525,285 B1 1/2020 Friedman
10,549,117 B2 2/2020 Vanderstraten et al.
10,603,514 B2 3/2020 Grittani et al.
10,609,806 B2 3/2020 Roecken et al.
10,636,609 B1 4/2020 Bertsche et al.
10,660,588 B2 5/2020 Boyd et al.
10,661,100 B2 5/2020 Shen
10,682,528 B2 6/2020 Ansorge et al.
10,702,716 B2 7/2020 Heese
10,758,746 B2 9/2020 Kwak et al.
10,870,018 B2 12/2020 Bartkoski et al.
11,986,677 B2 * 5/2024 Smith .................. A61N 5/1069
2005/0020917 A1 1/2005 Scherch
2006/0193435 A1 8/2006 Hara et al.
2007/0205373 A1 9/2007 Kornblau et al.
2007/0287878 A1 12/2007 Fantini et al.
2008/0002811 A1 1/2008 Allison
2008/0023644 A1 1/2008 Pedroni
2009/0063110 A1 3/2009 Failla et al.
2009/0287467 A1 11/2009 Sparks et al.
2010/0119032 A1 5/2010 Yan et al.
2010/0177870 A1 7/2010 Nord et al.
2010/0178245 A1 7/2010 Arnsdorf et al.
2010/0260317 A1 10/2010 Chang et al.
2011/0006224 A1 1/2011 Maltz et al.
2011/0091015 A1 4/2011 Yu et al.
2011/0135058 A1 6/2011 Sgouros et al.
2011/0176723 A1 7/2011 Ali et al.
2012/0076271 A1 3/2012 Yan et al.

(56) References Cited

U.S. PATENT DOCUMENTS

| | | | |
|---|---|---|---|
| 2012/0157746 | A1 | 6/2012 | Meltsner et al. |
| 2012/0171745 | A1 | 7/2012 | Itoh |
| 2012/0184841 | A1 | 7/2012 | Nielsen et al. |
| 2012/0197058 | A1 | 8/2012 | Shukla et al. |
| 2013/0116929 | A1 | 5/2013 | Carlton et al. |
| 2013/0150922 | A1 | 6/2013 | Butson et al. |
| 2013/0177641 | A1 | 7/2013 | Ghoroghchian |
| 2013/0231516 | A1 | 9/2013 | Loo et al. |
| 2014/0177807 | A1 | 6/2014 | Lewellen et al. |
| 2014/0185776 | A1 | 7/2014 | Li et al. |
| 2014/0206926 | A1 | 7/2014 | van der Laarse |
| 2014/0275706 | A1 | 9/2014 | Dean et al. |
| 2014/0369476 | A1 | 12/2014 | Harding |
| 2015/0011817 | A1 | 1/2015 | Feng |
| 2015/0202464 | A1 | 7/2015 | Brand et al. |
| 2015/0231411 | A1 | 8/2015 | O'Neal, III et al. |
| 2015/0306423 | A1 | 10/2015 | Bharat et al. |
| 2016/0213949 | A1 | 7/2016 | Uhlemann et al. |
| 2016/0279444 | A1 | 9/2016 | Schlosser |
| 2016/0310764 | A1 | 10/2016 | Bharadwaj et al. |
| 2017/0189721 | A1 | 7/2017 | Sumanaweera et al. |
| 2017/0203129 | A1 | 7/2017 | Dessy |
| 2017/0281973 | A1 | 10/2017 | Allen et al. |
| 2018/0021594 | A1 | 1/2018 | Papp et al. |
| 2018/0043183 | A1 | 2/2018 | Sheng et al. |
| 2018/0056090 | A1 | 3/2018 | Jordan et al. |
| 2018/0099154 | A1 | 4/2018 | Prieels |
| 2018/0099155 | A1 | 4/2018 | Prieels et al. |
| 2018/0099159 | A1 | 4/2018 | Forton et al. |
| 2018/0154183 | A1 | 6/2018 | Sahadevan |
| 2018/0197303 | A1 | 7/2018 | Jordan et al. |
| 2018/0207425 | A1 | 7/2018 | Carlton et al. |
| 2018/0236268 | A1 | 8/2018 | Zwart et al. |
| 2019/0022407 | A1 | 1/2019 | Abel et al. |
| 2019/0022422 | A1 | 1/2019 | Trail et al. |
| 2019/0054315 | A1 | 2/2019 | Isola et al. |
| 2019/0070435 | A1 | 3/2019 | Joe Anto et al. |
| 2019/0168027 | A1 | 6/2019 | Smith et al. |
| 2019/0255361 | A1 | 8/2019 | Mansfield |
| 2019/0299027 | A1 | 10/2019 | Fujii et al. |
| 2019/0299029 | A1 | 10/2019 | Inoue |
| 2019/0351259 | A1 | 11/2019 | Lee et al. |
| 2020/0001118 | A1 | 1/2020 | Snider et al. |
| 2020/0022248 | A1 | 1/2020 | Yi et al. |
| 2020/0030633 | A1 | 1/2020 | Van Heteren et al. |
| 2020/0035438 | A1 | 1/2020 | Star-Lack et al. |
| 2020/0069818 | A1 | 3/2020 | Jaskula-Ranga et al. |
| 2020/0164224 | A1 | 5/2020 | Vanderstraten et al. |
| 2020/0178890 | A1 | 6/2020 | Otto |
| 2020/0197730 | A1 | 6/2020 | Safavi-Naeini et al. |
| 2020/0254279 | A1 | 8/2020 | Ohishi |
| 2020/0269068 | A1 | 8/2020 | Abel et al. |
| 2020/0276456 | A1 | 9/2020 | Swerdloff |
| 2020/0282234 | A1 | 9/2020 | Folkerts et al. |

FOREIGN PATENT DOCUMENTS

| | | | |
|---|---|---|---|
| CN | 104884126 | A | 9/2015 |
| CN | 105102062 | A | 11/2015 |
| CN | 105792894 | A | 7/2016 |
| CN | 106730407 | A | 5/2017 |
| CN | 107362464 | A | 11/2017 |
| CN | 109966662 | A | 7/2019 |
| CN | 105169572 | B | 5/2020 |
| CN | 111481840 | A | 8/2020 |
| CN | 111481841 | A | 8/2020 |
| EA | 010207 | | 6/2008 |
| EP | 0979656 | A2 | 2/2000 |
| EP | 3338858 | A1 | 6/2018 |
| EP | 3384961 | A1 | 10/2018 |
| EP | 3421087 | A1 | 1/2019 |
| EP | 3453427 | A1 | 3/2019 |
| EP | 3586920 | A1 | 1/2020 |
| JP | 2617283 | B2 | 6/1997 |
| JP | 2019-097969 | A | 6/2019 |
| KR | 20050059245 | A | 6/2005 |
| WO | WO-2007/017177 | A1 | 2/2007 |
| WO | WO-2009/042952 | A1 | 4/2009 |
| WO | WO-2010/018476 | A2 | 2/2010 |
| WO | WO-2013/038240 | A1 | 3/2013 |
| WO | WO-2013/081218 | A2 | 6/2013 |
| WO | WO-2013/133936 | A1 | 9/2013 |
| WO | WO-2014/139493 | A1 | 9/2014 |
| WO | WO-2015/038832 | A1 | 3/2015 |
| WO | WO-2015/102680 | A2 | 7/2015 |
| WO | WO-2016/094284 | A1 | 6/2016 |
| WO | WO-2016/122957 | A1 | 8/2016 |
| WO | WO-2017/156316 | A1 | 9/2017 |
| WO | WO-2017/174643 | A1 | 10/2017 |
| WO | WO-2018/137772 | A1 | 8/2018 |
| WO | WO-2018/152302 | A1 | 8/2018 |
| WO | WO-2019/097250 | A1 | 5/2019 |
| WO | WO-2019/103983 | A1 | 5/2019 |
| WO | WO-2019/164835 | A1 | 8/2019 |
| WO | WO-2019/166702 | A1 | 9/2019 |
| WO | WO-2019/185378 | A1 | 10/2019 |
| WO | WO-2019/222436 | A2 | 11/2019 |
| WO | WO-2020/018904 | A1 | 1/2020 |
| WO | WO-2020/064832 | A1 | 4/2020 |
| WO | WO-2020/107121 | A1 | 6/2020 |
| WO | WO-2020/159360 | A1 | 8/2020 |

OTHER PUBLICATIONS

Ibrahim Oraiqat et al., "An Ionizing Radiation Acoustic Imaging (iRAI) Technique for Real- Time Dosimetric Measurements for FLASH Radiotherapy," Medical Physics, vol. 47, Issue10, Oct. 2020, pp. 5090-5101, First published: Jun. 27, 2020, https://doi.org/10.1002/mp.14358.

K. Petersson et al., "Dosimetry of ultra high dose rate irradiation for studies on the biological effect induced in normal brain and GBM," ICTR-PHE 2016, p. S84, Feb. 2016, https://publisher-connector.core.ac.uk/resourcesync/data/elsevier/pdf/14c/aHR0cDovL2FwaS51bHNIdmllci5jb20vY29udGVudC9hcnRpY2xlL3BpaS9zMDE2NzgxNDAxNjMwMTcyNA==.pdf.

Susanne Auer et al., "Survival of tumor cells after proton irradiation with ultra-high dose rates," Radiation Oncology 2011, 6:139, Published Oct. 18, 2011, DOI: https://doi.org/10.1186/1748-717X-6-139.

Cynthia E. Keen, "Clinical linear accelerator delivers FLASH radiotherapy," Physics World, Apr. 23, 2019, IOP Publishing Ltd, https://physicsworld.com/a/clinical-linear-accelerator-delivers-flash-radiotherapy/.

Fan et al., "Emission guided radiation therapy for lung and prostate cancers: A feasibility study on a digital patient," Med Phys. Nov. 2012; 39(11): 7140-7152. Published online Nov. 5, 2012. https://www.ncbi.nlm.nih.gov/pmc/articles/PMC3505203/doi: 10.1118/1.4761951.

Favaudon et al., "Ultrahigh dose-rate, "flash" irradiation minimizes the side-effects of radiotherapy," Cancer / Radiotherapy, vol. 19, Issues 6-7 , Oct. 2015 , pp. 526-531, Available online Aug. 12, 2015, https://doi.org/10.1016/j.canrad.2015.04.006.

O. Zlobinskaya et al., "The Effects of Ultra-High Dose Rate Proton Irradiation on Growth Delay in the Treatment of Human Tumor Xenografts in Nude Mice," Radiation Research, 181(2):177-183. Published Feb. 13, 2014, DOI: http://dx.doi.org/10.1667/RR13464.1.

Bjorn Zackrisson, "Biological Effects Of High Energy Radiation And Ultra High Dose Rates," Umea University Medical Dissertations, New series No. 315—ISSN 0346-6612, From the Department of Oncology, University of Umea, Umea, Sweden, ISBN 91-7174-614-5, Printed in Sweden by the Printing Office of Umea University, Umea, 1991.

P. Montay-Gruel et al., "Irradiation in a flash: Unique sparing of memory in mice after whole brain irradiation with dose rates above 100 Gy/s," Radiotherapy and Oncology, vol. 124, Issue 3, Sep. 2017, pp. 365-369, Available online May 22, 2017, doi: 10.1016/j.radonc.2017.05.003.

(56) References Cited

OTHER PUBLICATIONS

Bw Loo et al., "Delivery of Ultra-Rapid Flash Radiation Therapy and Demonstration of Normal Tissue Sparing After Abdominal Irradiation of Mice," International Journal of Radiation Oncology, Biology, Physics, vol. 98, Issue 2, p. E16, Supplement: S Meeting Abstract: P003, Published: Jun. 1, 2017, DOI: https://doi.org/10.1016/j.ijrobp.2017.02.101.

Bhanu Prasad Venkatesulu et al., "Ultra high dose rate (35 Gy/sec) radiation does not spare the normal tissue in cardiac and splenic models of lymphopenia and gastrointestinal syndrome," Sci Rep 9, 17180 (2019), Published Nov. 20, 2019, DOI: https://doi.org/10.1038/s41598-019-53562-y.

P. Montay-Gruel et al., "Long-term neurocognitive benefits of FLASH radiotherapy driven by reduced reactive oxygen species," PNAS May 28, 2019, vol. 116, No. 22, pp. 10943-10951; first published May 16, 2019, https://doi.org/10.1073/pnas.1901777116.

Peter G. Maxim et al., "FLASH radiotherapy: Newsflash or flash in the pan?", Medical Physics, 46 (10), Oct. 2019, pp. 4287-4290, American Association of Physicists in Medicine, First published: Jun. 27, 2019, https://doi.org/10.1002/mp. 13685.

Andrei Pugachev et al., "Pseudo beam's-eye-view as applied to beam orientation selection in intensity-modulated radiation therapy," Int. J. Radiation Oncology Biol. Phys., vol. 51, Issue 5, P1361-1370, Dec. 1, 2001, DOI: https://doi.org/10.1016/S0360-3016(01)01736-9.

Xiaodong Zhang et al., "Intensity-Modulated Proton Therapy Reduces the Dose to Normal Tissue Compared With Intensity-Modulated Radiation Therapy or Passive Scattering Proton Therapy and Enables Individualized Radical Radiotherapy for Extensive Stage IIIB Non-Small-Cell Lung Cancer: A Virtual Clinical Study," Int. J. Radiation Oncology Biol. Phys., vol. 77, No. 2, pp. 357-366, 2010, Available online Aug. 5, 2009, DOI: https://doi.org/10.1016/j.ijrobo.2009.04.028.

A.J. Lomax et al., "Intensity modulated proton therapy: A clinical example," Medical Physics, vol. 28, Issue 3, Mar. 2001, pp. 317-324, First published: Mar. 9, 2001, https://doi.org/10.1118/1.1350587.

Lamberto Widesott et al., "Intensity-Modulated Proton Therapy Versus Helical Tomotherapy in Nasopharynx Cancer: Planning Comparison and NTCP Evaluation," Int. J. Radiation Oncology Biol. Phys., vol. 72, No. 2, pp. 589-596, Oct. 1, 2008, Available online Sep. 13, 2008, DOI: https://doi.org/10.1016/j.ijrobp.2008.05.065.

Andrei Pugachev et al., "Role of beam orientation optimization in intensity-modulated radiation therapy," Int. J. Radiation Oncology Biol. Phys., vol. 50, No. 2, pp. 551-560, Jun. 1, 2001, Available online May 10, 2001, DOI: https://doi.org/10.1016/S0360-3016(01)01502-4.

Damien C. Weber et al., "Radiation therapy planning with photons and protons for early and advanced breast cancer: an overview," Radiat Oncol. 2006; 1: 22. Published online Jul. 20, 2006, doi: 10.1186/1748-717X-1-22.

RaySearch Laboratories, "Leading the way in cancer treatment, Annual Report 2013," RaySearch Laboratories (publ), Stockholm, Sweden, 94 pages, Apr. 2014, https://www.raysearchlabs.com/siteassets/about-overview/media-center/wp-re-ev-n-pdfs/brochures/raysearch-ar-2013-eng.pdf.

Fredrik Carlsson, "Utilizing Problem Structure in Optimization of Radiation Therapy," KTH Engineering Sciences, Doctoral Thesis, Stockholm, Sweden, Apr. 2008, Optimization and Systems Theory, Department of Mathematics, Royal Institute of Technology, Stockholm, Sweden, ISSN 1401-2294, https://www.raysearchlabs.com/globalassets/about-overview/media-center/wp-re-ev-n-pdfs/publications/thesis-fredrik_light.pdf.

Chang-Ming Charlie Ma, "Physics and Dosimetric Principles of SRS and SBRT," Mathews J Cancer Sci. 4(2): 22, 2019, published: Dec. 11, 2019, ISSN: 2474-6797, DOI: https://doi.org/10.30654/MJCS.10022.

Alterego-Admin, "Conventional Radiation Therapy May Not Protect Healthy Brain Cells," International Neuropsychiatric Association—INA, Oct. 10, 2019, https://inawebsite.org/conventional-radiation-therapy-may-not-protect-healthy-brain-cells/.

Aafke Christine Kraan, "Range verification methods in particle therapy: underlying physics and Monte Carlo modeling," Frontiers in Oncology, Jul. 7, 2015, vol. 5, Article 150, 27 pages, doi: 10.3389/fonc.2015.00150.

Wayne D. Newhauser et al., "The physics of proton therapy," Physics in Medicine & Biology, Mar. 24, 2015, 60 R155-R209, Institute of Physics and Engineering in Medicine, IOP Publishing, doi: 10. 1088/0031-9155/60/8/R155.

S E McGowan et al., "Treatment planning optimisation in proton therapy," Br J Radiol, 2013, 86, 20120288, The British Institute of Radiology, 12 pages, DOI: 10.1259.bjr.20120288.

Steven Van De Water et al., "Towards FLASH proton therapy: the impact of treatment planning and machine characteristics on achievable dose rates," Acta Oncologica, Jun. 26, 2019, vol. 58, No. 10, p. 1462-1469, Taylor & Francis Group, DOI: 10.1080/0284186X.2019.1627416.

J- Groen, "Flash optimisation in clinical IMPT treatment planning," MSC Thesis, Jul. 1, 2020, Erasmus University Medical Center, department of radiotherapy, Delft University of Technology, 72 pages.

Muhammad Ramish Ashraf et al., "Dosimetry for FLASH Radiotherapy: A Review of Tools and the Role of Radioluminescence and Cherenkov Emission," Frontiers in Oncology, Aug. 21, 2020, vol. 8, Article 328, 20 pages, doi: 10.3389/fphy.2020.00328.

Emil Schuler et al., "Experimental Platform for Ultra-high Dose Rate FLASH Irradiation of Small Animals Using a Clinical Linear Accelerator," International Journal of Radiation Oncology, Biology, Physics, vol. 97, No. 1, Sep. 2016, pp. 195-203.

Elette Engels et al., "Toward personalized synchrotron microbeam radiation therapy," Scientific Reports, 10:8833, Jun. 1, 2020, 13 pages, DOI: https://doi.org/10.1038/s41598-020-65729-z.

P-H Mackeprang et al., "Assessing dose rate distributions in VMAT plans" (Accepted Version), Accepted Version: https://boris.unibe.ch/92814/8/dose_rate_project_revised_submit.pdf Published Version: 2016, Physics in medicine and biology, 61(8), pp. 3208-3221. Institute of Physics Publishing IOP, published Mar. 29, 2016, https://boris.unibe.ch/92814/.

Xiaoying Liang et al., "Using Robust Optimization for Skin Flashing in Intensity Modulated Radiation Therapy for Breast Cancer Treatment: A Feasibility Study," Practical Radiation Oncology, vol. 10, Issue 1, p. 59-69, Published by Elsevier Inc., Oct. 15, 2019.

Alexei Trofimov et al., "Optimization of Beam Parameters and Treatment Planning for Intensity Modulated Proton Therapy," Technology in Cancer Research & Treatment, vol. 2, No. 5, Oct. 2003, p. 437-444, Adenine Press.

Vladimir Anferov, "Scan pattern optimization for uniform proton beam scanning," Medical Physics, vol. 36, Issue 8, Aug. 2009, pp. 3560-3567, First published: Jul. 2, 2009.

Ryosuke Kohno et al., "Development of Continuous Line Scanning System Prototype for Proton Beam Therapy," International Journal of Particle Therapy, Jul. 11, 2017, vol. 3, Issue 4, p. 429-438, DOI: 10.14338/IJPT-16-00017.1.

Wenbo Gu et al., "Integrated Beam Orientation and Scanning-Spot Optimization in Intensity Modulated Proton Therapy for Brain and Unilateral Head and Neck Tumors," Med Phys. Author manuscript; available in PMC Apr. 1, 2019 https://www.ncbi.nlm.nih.gov/pmc/articles/PMC5904040/ Published in final edited form as: Med Phys. Apr. 2018; 45(4): 1338-1350. Published online Mar. 1, 2018. doi: 10.1002/mp. 12788 Accepted manuscript online: Feb. 2, 2018.

Paul Morel et al., "Spot weight adaptation for moving target in spot scanning proton therapy," Frontiers in Oncology, May 28, 2015, vol. 5, Article 119, 7 pages, doi: 10.3389/fonc.2015.00119.

Simeon Nill et al., "Inverse planning of intensity modulated proton therapy," Zeitschrift fur Medizinische Physik, vol. 14, Issue 1, 2004, pp. 35-40, https://doi.org/10.1078/0939-3889-00198.

A. Lomax, "Intensity modulation methods for proton radiotherapy," Physics in Medicine & Biology, Jan. 1999, vol. 44, No. 1, pp. 185-205, doi: 10.1088/0031-9155/44/1/014.

(56) References Cited

OTHER PUBLICATIONS

M Kramer et al., "Treatment planning for heavy-ion radiotherapy: physical beam model and dose optimization," Physics in Medicine & Biology, 2000, vol. 45, No. 11, pp. 3299-3317, doi: 10.1088/0031-9155/45/11/313.
Harald Paganetti, "Proton Beam Therapy," Jan. 2017, Physics World Discovery, IOP Publishing Ltd, Bristol, UK, 34 pages, DOI: 10.1088/978-0-7503-1370-4.
Shinichi Shimizu et al., "A Proton Beam Therapy System Dedicated to Spot-Scanning Increases Accuracy with Moving Tumors by Real-Time Imaging and Gating and Reduces Equipment Size," PLoS ONE, Apr. 18, 2014, vol. 9, Issue 4, e94971, https://doi.org/10.1371/journal.pone.0094971.
Heng Li et al., "Reducing Dose Uncertainty for Spot-Scanning Proton Beam Therapy of Moving Tumors by Optimizing the Spot Delivery Sequence," International Journal of Radiation Oncology, Biology, Physics, vol. 93, Issue 3, Nov. 1, 2015, pp. 547-556, available online Jun. 18, 2015, https://doi.org/10.1016/j.ijrobp.2015.06.019.
Ion Beam Applications Sa, "Netherlands Proton Therapy Center Delivers First Clinical Flash Irradiation," Imaging Technology News, May 2, 2019, Wainscot Media, https://www.itnonline.com/content/netherlands-proton-therapy-center-delivers-first-clinical-flash-irradiation.
R. M. De Kruijff, "FLASH radiotherapy: ultra-high dose rates to spare healthy tissue," International Journal of Radiation Biology, 2020, vol. 96, No. 4, pp. 419-423, published online: Dec. 19, 2019, https://doi.org/10.1080/09553002.2020.1704912.
Mevion Medical Systems, "Focus On The Future: Flash Therapy," Press Releases, Sep. 16, 2019, https://www.mevion.com/newsroom/press-releases/focus-future-flash-therapy.
Joseph D. Wilson et al., "Ultra-High Dose Rate (FLASH) Radiotherapy: Silver Bullet or Fool's Gold?", Frontiers in Oncology, Jan. 17, 2020, vol. 9, Article 1563, 12 pages, doi: 10.3389/fonc.2019.01563.
David P. Gierga, "Is Flash Radiotherapy coming?", International Organization for Medical Physics, 2020, https://www.iomp.org/iomp-news2-flash-radiotherapy/.
Abdullah Muhammad Zakaria et al., "Ultra-High Dose-Rate, Pulsed (FLASH) Radiotherapy with Carbon lons: Generation of Early, Transient, Highly Oxygenated Conditions in the Tumor Environment," Radiation Research, Dec. 1, 2020, vol. 194, Issue 6, pp. 587-593, Radiation Research Society, Published: Aug. 27, 2020, doi: https://doi.org/10.1667/RADE-19-00015.1.
Yusuke Demizu et al., "Carbon lon Therapy for Early-Stage Non-Small-Cell Lung Cancer," BioMed Research International, vol. 2014, Article ID 727962, 9 pages, Hindawi Publishing Corporation, published: Sep. 11, 2014, https://doi.org/10.1155/2014/727962.
Ivana Dokic et al., "Next generation multi-scale biophysical characterization of high precision cancer particle radiotherapy using clinical proton, helium-, carbon- and oxygen ion beams," Oncotarget, Aug. 3, 20160, vol. 7, No. 35, pp. 56676-56689, published online: Aug. 1, 2016, doi: 10.18632/oncotarget. 10996.
Aetna Inc., "Proton Beam, Neutron Beam, and Carbon lon Radiotherapy," 2020, No. 0270, http:/fwww.aetna.com/cpb/medical/data/200_299/0270.html.
Nicholas W. Colangelo et al., "The Importance and Clinical Implications of FLASH Ultra-High Dose-Rate Studies for Proton and Heavy Ion Radiotherapy," Radiat Res. Author manuscript; available in PMC Jan. 1, 2021. https://www.ncbi.nlm.nih.gov/pmc/articles/PMC6949397/ Published in final edited form as: Radial Res. Jan. 2020; 193(1): 1-4. Published online Oct. 2, 20198. doi: 10.1667/RR15537.1.
Vincent Favaudon et al., "Ultrahigh dose-rate FLASH irradiation increases the differential response between normal and tumor tissue in mice," Science Translational Medicine, Jul. 16, 2014, vol. 6, Issue 245, 245ra93, American Association for the Advancement of Science, DOI: 10.1126/scitranslmed.3008973.
"FlashRad: Ultra-high dose-rate FLASH radiotherapy to minimize the complications of radiotherapy," 2014, https://siric.curie.fr/sites/default/files/atoms/files/flashrad.pdf.
Tami Freeman, "Flash radiotherapy: from preclinical promise to the first human treatment," Physics World, Aug. 6, 019, IOP Publishing Ltd, https://physicsworld.com/a/flash-radiotherapy-from-preclinical-promise-to-the-first-human-treatment/.
Intraop Medical, Inc., "IntraOp and Lausanne University Hospital Announce Collaboration in FLASH radiotherapy," Jun. 18, 2020, https://intraop.com/news-events/lausanne-university-flash-radiotherapy-collaboration/.
M.-C. Vozenin et al., "Biological Benefits of Ultra-high Dose Rate FLASH Radiotherapy: Sleeping Beauty Awoken," Clin Oneal (R Coll Radial). Author manuscript; available in PMC Nov. 12, 2019. https://www.ncbi.nlm.nih.gov/pmc/articles/PMC6850216/ Published in final edited form as: Clin Oneal (R Coll Radial). Jul. 2019; 31(7): 407-415. Published online Apr. 19, 2019. doi: 10.1016/j.clon.2019.04.001.
Efstathios Kamperis et al., "A Flash back to radiotherapy's past and then fast forward to the future," J Cancer Prev Curr Res. 2019;10(6):142-144. published Nov. 13, 2019, DOI: 10.15406/jcpcr.2019.10.00407.
P. Symonds et al., "FLASH Radiotherapy: The Next Technological Advance in Radiation Therapy?", Clinical Oncology, vol. 31, Issue 7, P405-406, Jul. 1, 2019, The Royal College of Radiologists, Published by Elsevier Ltd., DOI: https://doi.org/10.1016/j.clon.2019.05.011.
Swati Girdhani et al., "Abstract LB-280: Flash: A novel paradigm changing tumor irradiation platform that enhances therapeutic ratio by reducing normal tissue toxicity and activating immune pathways," Proceedings: AACR Annual Meeting 2019; Mar. 29-Apr. 3, 2019; Atlanta, GA, published Jul. 2019, vol. 79, Issue 13 Supplement, pp. LB-280, American Association for Cancer Research, DOI: https://doi.org/10.1158/1538-7445.AM2019-LB-280.
Bazalova-Carter et al., "On the capabilities of conventional x-ray tubes to deliver ultra-high (FLASH) dose rates," Med. Phys. Dec. 2019; 46 (12):5690-5695, published Oct. 23, 2019, American Association of Physicists in Medicine doi: 10.1002/mp.13858. Epub Oct. 23, 2019. PMID: 31600830.
Manuela Buonanno et al., "Biological effects in normal cells exposed to FLASH dose rate protons," Radiother Oncol. Author manuscript; available in PMC Oct. 1, 2020. https://www.ncbi.nlm.nih.gov/pmc/articles/PMC6728238/ Published in final edited form as: Radiother Oncol. Oct. 2019; 139: 51-55. Published online Mar. 5, 2019. doi: 10.1016/j.radonc.2019.02.009.
N. Rama et al., "Improved Tumor Control Through T-cell Infiltration Modulated by Ultra-High Dose Rate Proton FLASH Using a Clinical Pencil Beam Scanning Proton System," International Journal of Radiation Oncology, Biology, Physics, vol. 105, Issue 1, Supplement, S164-S165, Sep. 1, 2019, Mini Oral Sessions, DOI: https://doi.org/10.1016/j.ijrobp.2019.06.187.
Inserm Press Office, "Radiotherapy 'flashes' to reduce side effects," Press Release, Jul. 16, 2014, https://presse.inserm.fr/en/radiotherapy-flashes-to-reduce-side-effects/13394/.
Eric S. Diffenderfer et al., "Design, Implementation, and in Vivo Validation of a Novel Proton FLASH Radiation Therapy System," International Journal of Radiation Oncology, Biology, Physics, vol. 106, Issue 2, Feb. 1, 2020, pp. 440-448, Available online Jan. 9, 2020, Published by Elsevier Inc., DOI: https://doi.org/10.1016/j.ijrobp.2019.10.049.
Valerie Devillaine, "Radiotherapy and Radiation Biology," Institut Curie, Apr. 21, 2017, https://institut-curie.org/page/radiotherapy-and-radiation-biology.
Imaging Technology News, "ProNova and medPhoton to Offer Next Generation Beam Delivery, Advanced Imaging for Proton Therapy," Oct. 6, 2014, Wainscot Media, Link: https://www.itnonline.com/content/pronova-and-medphoton-offer-next-generation-beam-delivery-advanced-imaging-proton-therapy.
Oncolink Team, "Radiation Therapy: Which type is right for me?", OncoLink Penn Medicine, last reviewed Mar. 3, 2020, Trustees of the University of Pennsylvania, https://www.oncolink.org/cancer-treatment/radiation/introduction-to-radiation-therapy/radiation-therapy-which-type-is-right-for-me.

(56) References Cited

OTHER PUBLICATIONS

Marco Durante et al., "Faster and safer? FLASH ultra-high dose rate in radiotherapy," Br J Radiol 2018; 91(1082): Jun. 28, 2017, British Institute of Radiology, Published Online: Dec. 15, 2017, https://doi.org/10.1259/bjr-20170628.
John R. Fischer, "PMB launches FLASH radiotherapy system for use in clinical trials," HealthCare Business News, Jun. 29, 2020, DOTmed.com, Inc., https://www.dotmed.com/news/story/51662.
Marie-Catherine Vozenin et al., "The advantage of FLASH radiotherapy confirmed in mini-pig and cat-cancer patients," Clinical Cancer Research, Author Manuscript Published OnlineFirst Jun. 6, 2018, https://clincancerres.aacrjournals.org/content/clincanres/early/2018/06/06/1078-0432 .CCR-17-3375full.pdf.

* cited by examiner

600

TRIGGERED TREATMENT SYSTEMS AND METHODS

CROSS-REFERENCE TO RELATED APPLICATIONS

This is a continuation application of U.S. patent application Ser. No. 17/132,966 entitled "Triggered Treatment Systems and Methods", by Christel Smith et al., filed Dec. 23, 2020, which is a continuation of U.S. application Ser. No. 16/237,502 entitled "Triggered Treatment Systems and Methods", by Christel Smith et al., filed Dec. 31, 2018, now U.S. Pat. No. 10,898,730, which is a continuation application of U.S. patent application Ser. No. 15/657,072, now U.S. Pat. No. 10,183,179, entitled "Triggered Treatment Systems and Methods", by Christel Smith et al., filed Jul. 21, 2017, the entire contents of each of which are hereby incorporated by reference.

BACKGROUND

The use of radiation therapy to treat cancer is well known. Typically, radiation therapy involves directing a beam of high energy proton, photon, ion, or electron radiation ("therapeutic radiation") into a target or target volume (e.g., a tumor or lesion) in a patient.

Before a patient is treated with radiation, a treatment plan specific to that patient is developed. The plan defines various aspects of the therapy using simulations and optimizations based on past experiences. In general, the purpose of the treatment plan is to deliver sufficient radiation to the target while minimizing exposure of surrounding normal, healthy tissue to the radiation.

The planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one plan that is best suited to achieving the desired outcome.

A recent radiobiology study has demonstrated the effectiveness of delivering an entire, relatively high therapeutic radiation dose to a target within a single, short period of time. This type of treatment is referred to generally herein as FLASH radiation therapy (FLASH RT). Evidence to date suggests that FLASH RT advantageously spares normal, healthy tissue from damage when that tissue is exposed to only a single irradiation for only a very short period of time. FLASH RT thus introduces important constraints that are not considered in or achieved with conventional radiation treatment planning.

Typically for radiation therapy treatment, a patient first receives a CT (computed tomography) scan used to simulate the patient's treatment. A simulated treatment plan defines beam orientations and corresponding particle fluences to generate a 3D (three-dimensional) dose distribution that best achieves the physician's prescription and/or intent. Once the treatment plan has been defined, treatment can commence. It is noted that treatment uncertainties result from differences in the patient appearance at each treatment fraction compared to the CT simulation from which the treatment plan was derived. In addition, organ motion related to gross patient movement, breathing, heart function, and variable organ filling further compounds the treatment uncertainty.

Various techniques are currently employed to manage organ motion in order to minimize the difference between the planned and delivered dose to the patient, including: breath holding, treatment gating, or abdominal compression. Each of these techniques has associated benefits and drawbacks, but all are designed to manage motion when treatment delivery time is over several minutes and may last as long as 60 minutes.

For example, one of the disadvantages of breath holding is that many patients do not have lung function to hold their breath for more than a few seconds; therefore, precluding them from holding their breath for the duration of an entire treatment field. It is noted that one of the disadvantages associated with treatment gating is that it requires continuous monitoring of the patient during relatively lengthy treatments, and turning the treatment beam off whenever the target volume moves outside of a predetermined volume of interest. Furthermore, treatment gating may increase the treatment time considerably, because the treatment beam may be held off for large periods of the breathing cycle. Note that abdominal compression is often poorly tolerated by most patients, as it places patients in a great deal of discomfort and can limit critical functions associated with normal organ motion, such as breathing or bowel motion.

SUMMARY

Various embodiments in accordance with the present disclosure can address the disadvantages described above.

In various embodiments, the present disclosure provides a triggered treatment which is a new paradigm of Image Guided Radiation Therapy that nearly eliminates organ motion during radiation delivery. In various embodiments, by delivering the entire treatment from each beam in a flash lasting a short period of time (e.g., a fraction of a second), target and organ motion is relatively "frozen" in 3D (three-dimensional) space and treatment uncertainty caused by motion is minimized. A method in accordance with various embodiments involves monitoring motion of the target volume of a patient before treatment, and selecting the appropriate time to trigger the flash of treatment. For each beam orientation, a region of interest can be monitored in real-time fluoroscopic projections through the patient. A single or multiple simultaneous fluoroscopic images can localize the target in three dimensions as it moves within the patient. When the target position matches its location within a pre-treatment simulation (e.g., CT (computed tomography), MRI (magnetic resonance imaging), or any medical imaging), the triggered treatment can be delivered precisely to the target in a nearly instantaneous flash.

In various embodiments, the triggered treatment of the present disclosure can include monitoring patient motion in real-time using fluoroscopic imaging (or alternate methods), which allows the patient to breathe freely or to hold their breath if indicated. In addition, this preserves patient comfort, ultimately making the patient experience more positive. Furthermore, it is noted that treatment margins that account for motion uncertainty can be markedly reduced due to the ultra-short triggered treatment flash, meaning that substantially less healthy tissue is irradiated, which should result in less side-effects and late toxicities resulting from the treatment.

In various embodiments, the triggered treatment of the present disclosure can include monitoring the patient surface continuously and triggering a sequence of radiographic images to be acquired to confirm the position of the target before triggering the treatment.

In various embodiments, the triggered treatment of the present disclosure can include any method of continuously tracking patient motion and/or breathing combined with some form of visualizing internal anatomy, fiducial markers, or surrogates of internal anatomy.

In various embodiments, the triggered treatment of the present disclosure can be implemented with any particle or wave radiation delivered at FLASH dose rates (e.g., greater than 40 Gy (grays)/second), but is not limited to such.

In various embodiments, in accordance with the present disclosure, it is noted that fluoroscopy (e.g., ionizing radiation) dose can be used with standard dose rates to reconstruct dose for inter-fractional dose tracking.

In various embodiments, a radiation therapy method can include loading a planning image of a target in a human. In addition, a four-dimensional (4D) real-time video image can be generated of the target. A computation can be made of an occurrence of substantial alignment between the target of the 4D real-time video image and the target of the planning image. Furthermore, after the computing, a beam of radiation is triggered to deliver a dosage to the target in a short period of time (e.g., less than a second).

In various embodiments, a radiation therapy method can include loading a planning image of a target in a human. Moreover, a 4D real-time video image can be generated of the target. A mapping can be performed of the target in both the 4D real-time video image and the planning image. A computation can be made of an occurrence of substantial alignment between the target of the 4D real-time video image and the target of the planning image. Additionally, after the computing, a beam of radiation is triggered to deliver a fraction of a dosage to the target in a short period of time (e.g., less than a second).

In various embodiments, a radiation therapy method can include loading a planning image of a target in a human. A 4D real-time video image can be generated of the target. In addition, a computation can be made of an occurrence of substantial alignment between the target of the 4D real-time video image and the target of the planning image. After the computing, a beam of radiation is triggered to deliver a dosage to the target in a short period of time (e.g., less than a second). Moreover, after the triggering, quality assurance is performed utilizing imaging information associated with the 4D real-time video image.

In various embodiments, a radiation therapy method can include loading a planning image of a target in a human. In addition, the position of the target can be monitored. A computation can be made of an occurrence of substantial alignment between the position of the target and the target of the planning image. Furthermore, after the computing, a beam of radiation is triggered to deliver a dosage to the target in less than a second.

In various embodiments, a radiation therapy method can include loading a planning image of a target in a human. Moreover, the position of the target can be monitored. A mapping can be performed of the target in both the monitoring and the planning image. A computation can be made of an occurrence of substantial alignment between the position of the target and the target of the planning image. Additionally, after the computing, a beam of radiation is triggered to deliver a fraction of a dosage to the target in less than a second.

In various embodiments, a radiation therapy method can include loading a planning image of a target in a human. The position of the target can be monitored. In addition, a computation can be made of an occurrence of substantial alignment between the position of the target and the target of the planning image. After the computing, a beam of radiation is triggered to deliver a dosage to the target in less than a second. Moreover, after the triggering, quality assurance is performed utilizing information associated with the monitoring.

While various embodiments in accordance with the present disclosure have been specifically described within this Summary, it is noted that the claimed subject matter are not limited in any way by these various embodiments.

BRIEF DESCRIPTION OF THE DRAWINGS

Within the accompanying drawings, various embodiments in accordance with the present disclosure are illustrated by way of example and not by way of limitation. It is noted that like reference numerals denote similar elements throughout the drawings.

DETAILED DESCRIPTION

Figure 1:
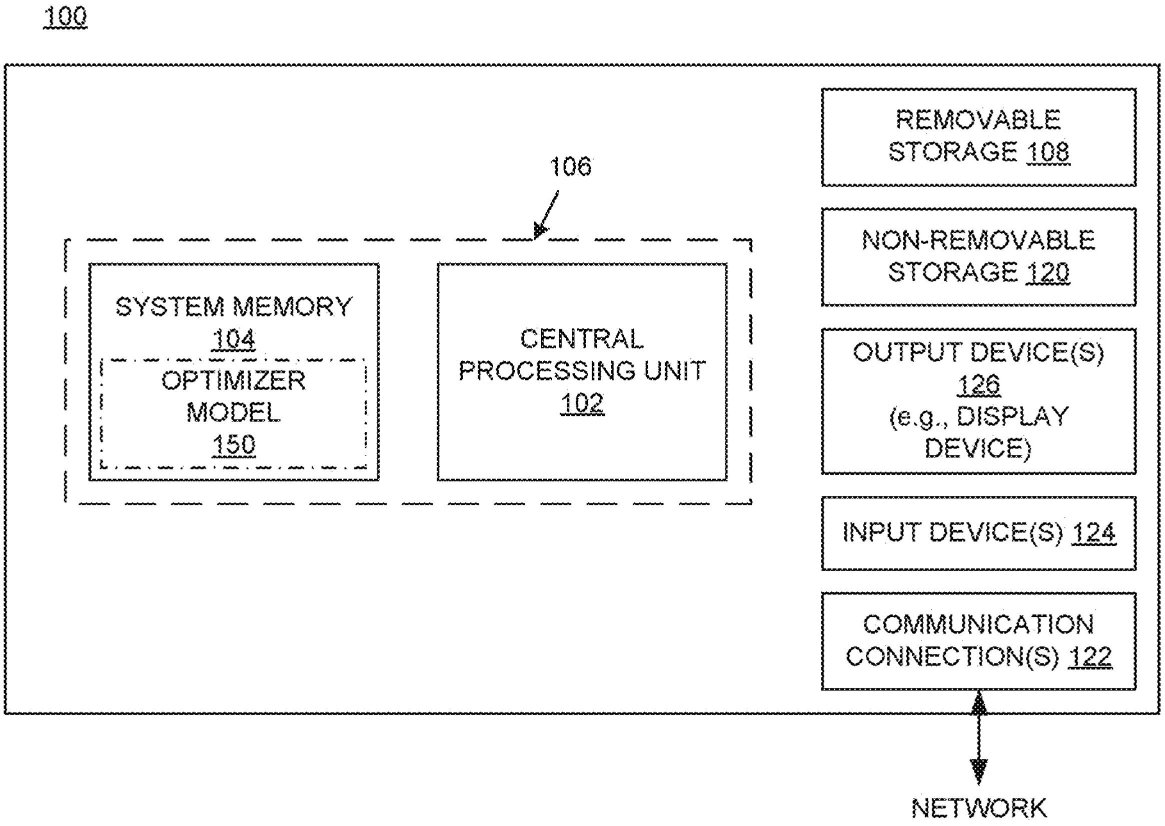
FIG. 1 is a block diagram of an example of a computing system upon which various embodiments described herein may be implemented in accordance with various embodiments of the present disclosure.

Reference will now be made in detail to various embodiments in accordance with the present disclosure, examples of which are illustrated in the accompanying drawings. While described in conjunction with various embodiments, it will be understood that these various embodiments are not intended to limit the present disclosure. On the contrary, the present disclosure is intended to cover alternatives, modifications and equivalents, which may be included within the scope of the present disclosure as construed according to the Claims. Furthermore, in the following detailed description of various embodiments in accordance with the present disclosure, numerous specific details are set forth in order to provide a thorough understanding of the present disclosure. However, it will be evident to one of ordinary skill in the art that the present disclosure may be practiced without these specific details or with equivalents thereof. In other instances, well known methods, procedures, components, and circuits have not been described in detail as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computing system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "determining," "accessing," "directing," "controlling," "defining," "arranging," "generating," "acquiring," "triggering", "computing", "loading" or the like, refer to actions and processes of a computing system or similar electronic computing device or processor (e.g., the computing system 100 of FIG. 1). The computing system or similar electronic computing device manipulates and transforms data represented as physical (electronic) quantities within the computing system memories, registers or other such information storage, transmission or display devices. Terms such as "dose" or "fluence" generally refer to a dose or fluence value; the use of such terms will be clear from the context of the surrounding discussion.

Portions of the detailed description that follows are presented and discussed in terms of a method. Although steps and sequencing thereof are disclosed in figures herein describing the operations of this method, such steps and sequencing are exemplary. Any method is well suited to performing various other steps or variations of the steps recited in the flowchart of the figure herein, and in a sequence other than that depicted and described herein.

Various embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can be accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 shows a block diagram of an example of a computing system 100 upon which various embodiments described herein may be implemented in accordance with various embodiments of the present disclosure. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., are also included.

In the example of FIG. 1, the memory 104 includes computer-readable instructions, data structures, program modules, and the like associated with an "optimizer" model 150. However, the optimizer model 150 may instead reside in any one of the computer storage media used by the system 100, or may be distributed over some combination of the computer storage media, or may be distributed over some combination of networked computers. The functionality of the optimizer model 150 is described below.

It is noted that the computing system 100 may not include all of the elements illustrated by FIG. 1. In addition, the computing system 100 can be implemented to include one or more elements not illustrated by FIG. 1. It is pointed out that the computing system 100 can be utilized or implemented in any manner similar to that described and/or shown by the present disclosure, but is not limited to such.

Figure 2:
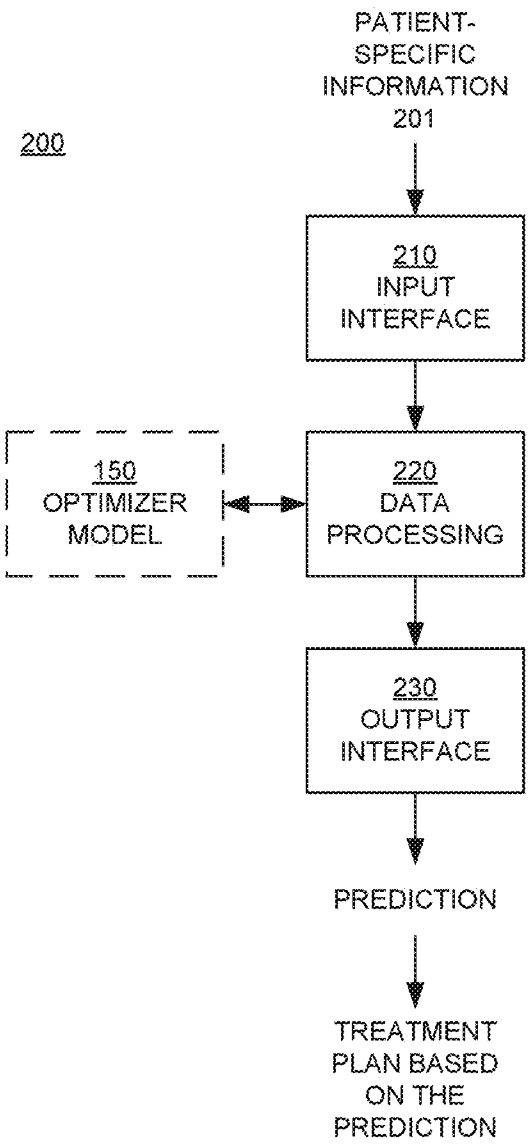
FIG. 2 is a block diagram illustrating an example of an automated radiation therapy treatment planning system in accordance with various embodiments of the present disclosure.

FIG. 2 is a block diagram illustrating an example of an automated radiation therapy treatment planning system 200 in accordance with various embodiments of the present disclosure. The system 200 includes an input interface 210 to receive patient-specific information (data) 201, a data processing component 220 that implements the optimizer model 150, and an output interface 230. The system 200 in whole or in part may be implemented as a software program, hardware logic, or a combination thereof on/using the computing system 100 (FIG. 1).

In the example of FIG. 2, the patient-specific information is provided to and processed by the optimizer model 150.

The optimizer model 150 yields a prediction result. A treatment plan based on the prediction result can then be generated.

Note that the system 200 may not include all of the elements illustrated by FIG. 2. Furthermore, the system 200 can be implemented to include one or more elements not illustrated by FIG. 2. It is pointed out that the system 200 can be utilized or implemented in any manner similar to that described and/or shown by the present disclosure, but is not limited to such.

Figure 3:
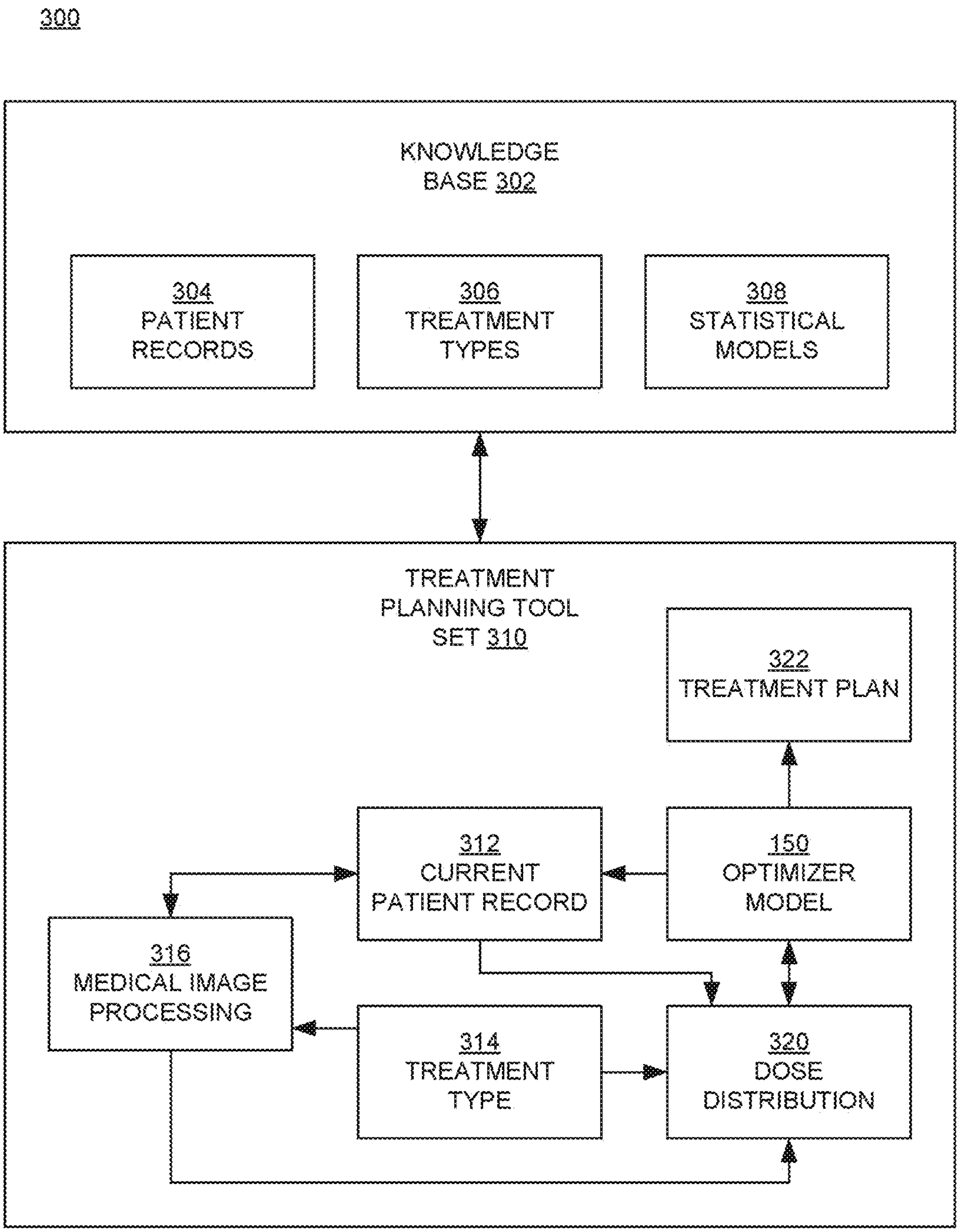
FIG. 3 illustrates a knowledge-based planning system in accordance with various embodiments of the present disclosure.

FIG. 3 illustrates a knowledge-based planning system 300 in accordance with various embodiments of the present disclosure. In the example of FIG. 3, the system 300 includes a knowledge base 302 and a treatment planning tool set 310. The knowledge base 302 includes patient records 304 (e.g., radiation treatment plans), treatment types 306, and statistical models 308. The treatment planning tool set 310 in the example of FIG. 3 includes a current patient record 312, a treatment type 314, a medical image processing module 316, the optimizer model (module) 150, a dose distribution module 320, and a final radiation treatment plan 322.

The treatment planning tool set 310 searches through the knowledge base 302 (through the patient records 304) for prior patient records that are similar to the current patient record 312. The statistical models 308 can be used to compare the predicted results for the current patient record 312 to a statistical patient. Using the current patient record 312, a selected treatment type 306, and selected statistical models 308, the tool set 310 generates a radiation treatment plan 322.

More specifically, in FIG. 3, based on past clinical experience, when a patient presents with a particular diagnosis, stage, age, weight, sex, co-morbidities, etc., there can be a treatment type that is used most often. By selecting the treatment type that the planner has used in the past for similar patients, a first-step treatment type 314 can be chosen. The medical image processing module 316 provides automatic contouring and automatic segmentation of two-dimensional cross-sectional slides (e.g., from computed tomography (CT), magnetic resonance imaging (MRI), or other medical imaging) to form a three-dimensional (3D) image using the medical images in the current patient record 312. Dose distribution maps are calculated by the dose distribution module 320, which may utilize the optimizer model 150.

In various embodiments according to the present disclosure, the optimizer model 150 uses a dose prediction model to help shape the dose distribution. The optimizer model 150 can provide, for example, a 3D dose distribution, fluences, and associated dose-volume histograms for the current patient.

It is pointed out that the system 300 may not include all of the elements illustrated by FIG. 3. Moreover, the system 300 can be implemented to include one or more elements not illustrated by FIG. 3. Note that the system 300 can be utilized or implemented in any manner similar to that described and/or shown by the present disclosure, but is not limited to such.

Figure 4A:
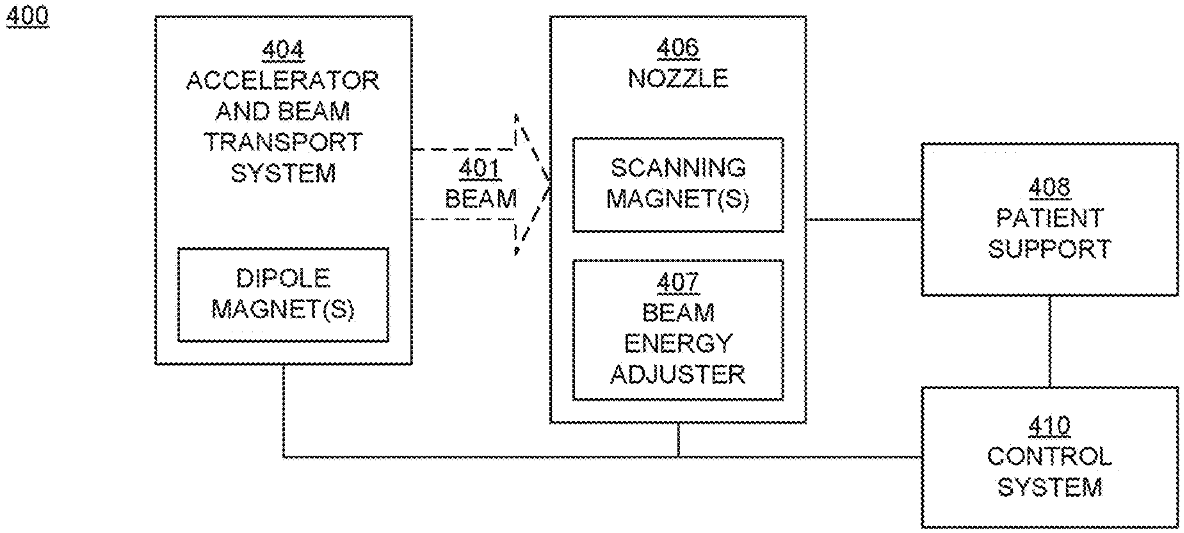
FIG. 4A is a block diagram showing selected components of a radiation therapy system upon which various embodiments can be implemented in accordance with various embodiments of the present disclosure.

FIG. 4A is a block diagram showing selected components of a radiation therapy system 400 upon which various embodiments can be implemented in accordance with various embodiments of the present disclosure. In the example of FIG. 4A, the system 400 includes an accelerator and beam transport system 404 and a nozzle 406.

The accelerator and beam transport system 404 generates and accelerates a beam of charged particles, such as electrons, protons, and ions (e.g., heavy ions), and contains the particles in a well-defined beam. In various embodiments, the accelerator is an isochronous cyclotron capable of continuous wave output. The accelerator (e.g., the cyclotron) extracts particles with a specified energy. This provides a high, continuous wave beam current for the high dose rate per shot. Other types of radio frequency accelerators can be used, such as a pulsed proton accelerator such as a synchrocyclotron, a synchrotron, a coupled cavity linear accelerator in addition to non-radio frequency accelerators, such as constant field, and laser-based accelerators. The accelerator (e.g., cyclotron) can be a lower power output cyclotron, such as a cyclotron that accelerates particles to the range of 70-300 million electron volts (MeVs).

Within FIG. 4A, the accelerator and beam transport system 404 includes components (e.g., dipole magnets, also known as bending magnets) that direct (e.g., bend, steer, or guide) the beam through the accelerator and beam transport system in a direction toward and into the nozzle 406. The accelerator and beam transport system 404 may also include one or more multileaf collimators (MLCs); each MLC leaf can be independently moved back-and-forth by the control system 410 to dynamically shape an aperture through which the beam can pass, to block or not block portions of the beam and thereby control beam shape and exposure time. The accelerator and beam transport system 404 may also include components that are used to adjust the beam energy entering the nozzle 406 so that it is different from the beam energy extracted from the accelerator. In various embodiments, sets of quadrupole magnets are located along the beam paths in the accelerator and beam transport system 404.

In various embodiments, it is noted that the accelerator and beam transport system 404 of the therapy system 400 can be implemented to produce any type of particle beam. For example, in various embodiments, the accelerator and beam transport system 404 can be implemented to produce any type of charged particle beam or non-charged particle beam. It is noted that in various embodiments the accelerator and beam transport system 404 can produce a particle beam of, but not limited to, electrons, protons, photons, carbon, carbon ions, neutrons, helium, alpha particles, oxygen, helium nuclei, or X-rays. In addition, in various embodiments, the accelerator and beam transport system 404 can be implemented to produce an ultra-sound output.

The nozzle 406 is used to aim the beam toward various locations (a target) within an object (e.g., a patient) supported on the patient support device 408 (e.g., a chair or table) in a treatment room. A target may be an organ, a portion of an organ (e.g., a volume or region within the organ), a tumor, diseased tissue, or a patient outline. In various embodiments, the nozzle 406 also includes components (e.g., X-Y scanning magnets) that steer (e.g., guide, deflect, or scan) the beam particles in the X and Y directions, to scan a target in a patient on the patient support device 408.

Within FIG. 4A, the nozzle 406 may be mounted on or a part of a gantry (e.g., FIGS. 4B, 4C, and 4D) that can be moved relative to the patient support device 408, which may also be moveable. In various embodiments, the accelerator and beam transport system 404 is also mounted on or is a part of the gantry; in various embodiments, the accelerator and beam transport system is separate from (but in communication with) the gantry.

The control system 410 of FIG. 4A receives and implements a prescribed treatment plan. In various embodiments, the control system 410 includes a computer system having a processor, memory, an input device (e.g., a keyboard), and perhaps a display in well-known fashion. The control system

410 can receive data regarding operation of the system 400. The control system 410 can control parameters of the accelerator and beam transport system 404, nozzle 406, and patient support device 408, including parameters such as the energy, intensity, direction, size, and/or shape of the beam, according to data it receives and according to the prescribed treatment plan.

As noted above, the particles entering the nozzle 406 have a specified energy. Thus, in various embodiments according to the present disclosure, the nozzle 406 includes one or more components that affect (e.g., decrease, modulate) the energy, intensity, or both energy and intensity of the particles in the beam. The term "beam modulator" is used herein as a general term for a component or components that affect the energy, intensity, or both energy and intensity of the particles in the beam, in order to control the range of the beam (e.g., the extent that the beam penetrates into a target) and/or to control the depth dose curve of the beam (e.g., the location of the maximal dose value in the target). In various embodiments, the beam modulator 407 includes a range modulator, a range shifter, an intensity modulator, or any combination thereof (e.g., a range modulator and a range shifter, a range and intensity modulator, etc.). That is, when the term "beam modulator" is used, then the element being discussed may be a range modulator, an intensity modulator, a range shifter, or both a range modulator and a range shifter, or a range and intensity modulator, or intensity modulator, or intensity modulator and range shifter. Examples of beam modulators are disclosed in the co-pending patent application, U.S. application Ser. No. 15/089,330, now U.S. Pat. No. 9,855, 445, entitled "Radiation Therapy Systems and Methods for Delivering Doses to a Target Volume"; however, the present disclosure is not so limited.

Note that the system 400 may not include all of the elements illustrated by FIG. 4A. In addition, the system 400 can be implemented to include one or more elements not illustrated by FIG. 4A. It is pointed out that the system 400 can be utilized or implemented in any manner similar to that described and/or shown by the present disclosure, but is not limited to such.

Figure 4B:
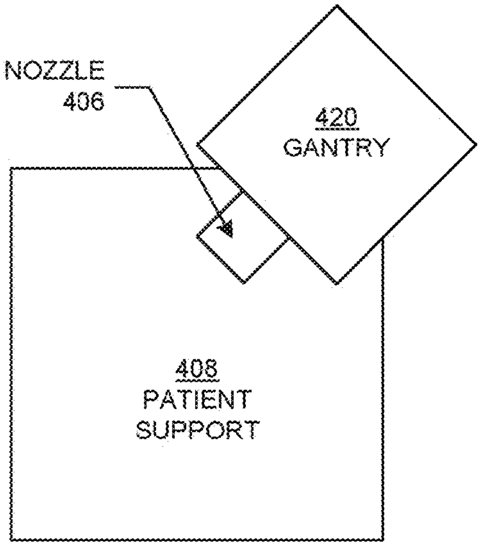
FIG. 4B is a block diagram illustrating a non-coplanar arrangement of a gantry and nozzle relative to a patient support device in accordance with various embodiments of the present disclosure.
Figure 4C:
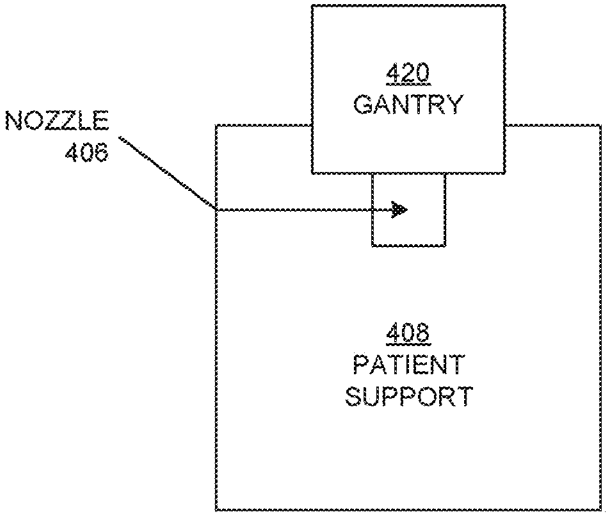
FIG. 4C is a block diagram illustrating a coplanar arrangement of a gantry and nozzle relative to a patient support device in accordance with various embodiments of the present disclosure.
Figure 4D:
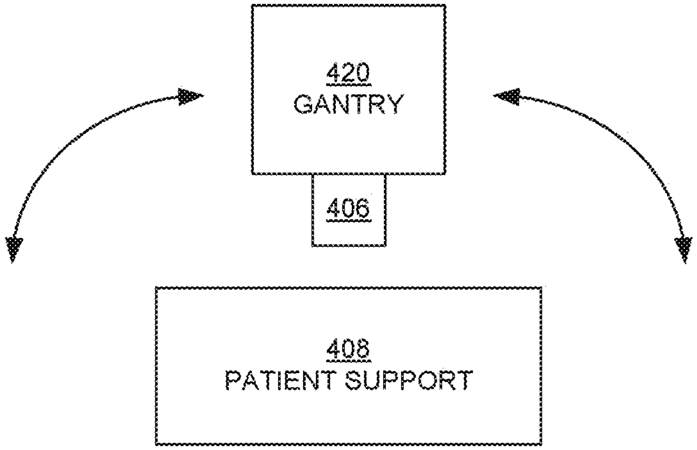
FIG. 4D is a block diagram illustrating movement of a gantry and nozzle around a patient support device in accordance with various embodiments of the present disclosure.

FIG. 4B is a block diagram illustrating a non-coplanar arrangement of a gantry 420 and nozzle 406 relative to a patient support device 408 in accordance with various embodiments of the present disclosure. FIG. 4C is a block diagram illustrating a coplanar arrangement of a gantry 420 and nozzle 406 relative to a patient support device 408 in accordance with various embodiments of the present disclosure. FIG. 4D is a block diagram illustrating movement of the gantry 420 and nozzle 406 around the patient support device 408 in accordance with various embodiments of the present disclosure. This movement can occur in either the non-coplanar arrangement or the coplanar arrangement.

Figure 5:
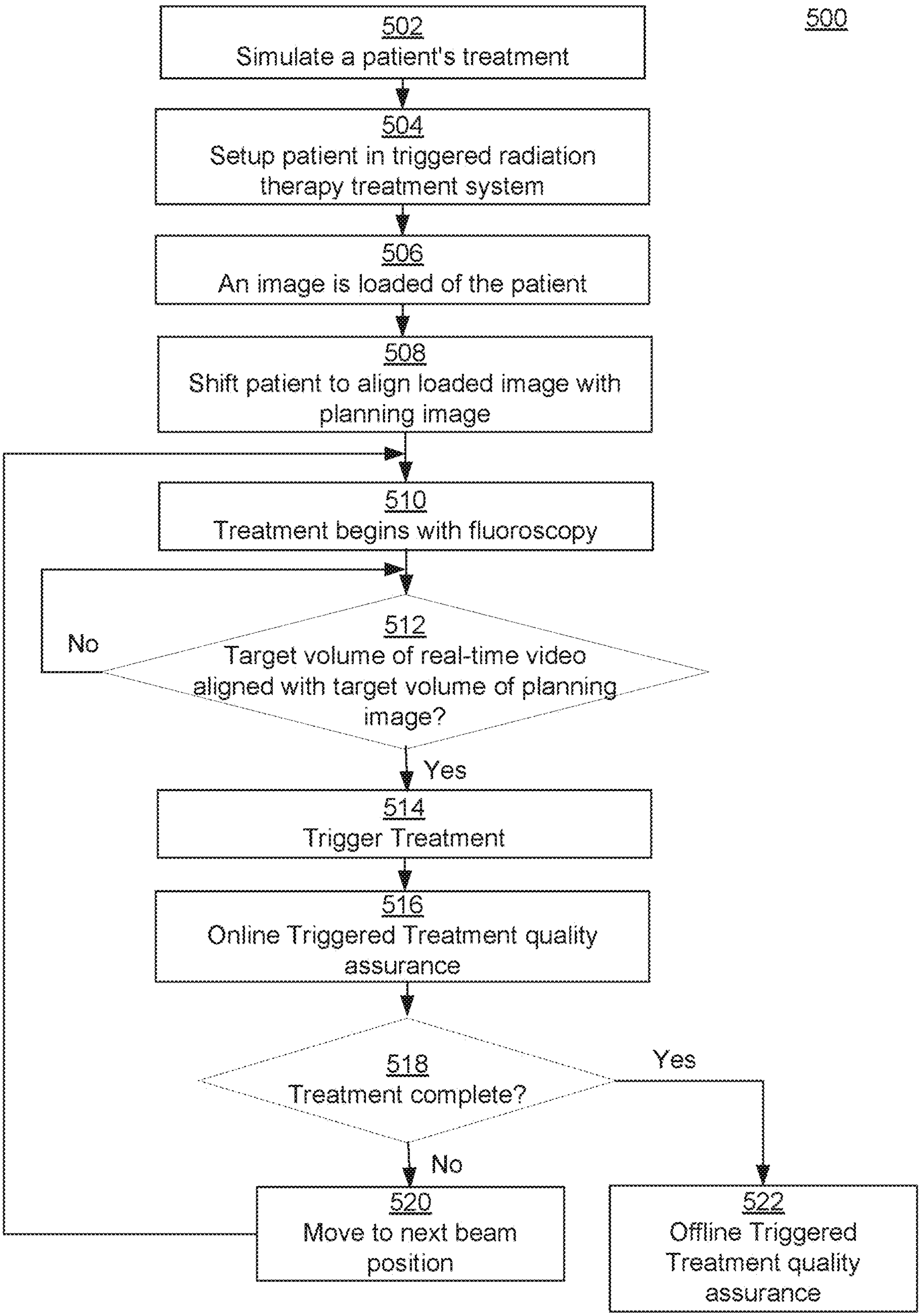
FIG. 5 is a flow diagram of a method in accordance with various embodiments of the present disclosure.

FIG. 5 is a flow diagram of a method 500 for performing triggered radiation therapy treatment in accordance with various embodiments of the present disclosure. Although specific operations are disclosed in FIG. 5, such operations are examples. The method 500 may not include all of the operations illustrated by FIG. 5. Also, method 500 may include various other operations and/or variations of the operations shown. Likewise, the sequence of the operations of flow diagram 500 can be modified. It is appreciated that not all of the operations in flow diagram 500 may be performed. In various embodiments, one or more of the operations of method 500 can be controlled or managed by software, by firmware, by hardware or by any combination thereof, but is not limited to such. Method 500 can include processes of various embodiments of the present disclosure which can be controlled or managed by a processor(s) and electrical components under the control of computer or computing device readable and executable instructions or code (e.g., the optimizer model 150 of FIG. 1). The computer or computing device readable and executable instructions (or code) may reside, for example, in data storage features such as computer or computing device usable volatile memory, computer or computing device usable non-volatile memory, and/or computer or computing device usable mass data storage. However, the computer or computing device readable and executable instructions (or code) may reside in any type of computer or computing device readable medium or memory (e.g., like those found within the computing system 100 of FIG. 1).

At operation 502, simulate a patient's treatment. Note that operation 502 can be implemented in a wide variety of ways. For example, in various embodiments, operation 502 can include the patient receiving a scan (e.g., CT (computed tomography), MRI (magnetic resonance imaging), or other medical imaging) of one or more target volumes used to simulate the patient's treatment. In various embodiments, the scan(s) at operation 502 can be referred to as a planning image(s) and can be loaded into one or more computing system memory devices. It is noted that operation 502 can be implemented in any manner similar to that described and/or shown by the present disclosure, but is not limited to such.

At operation 504 of FIG. 5, a patient is setup within a triggered radiation therapy treatment system. It is noted that operation 504 can be implemented in a wide variety of ways. For example, in various embodiments, the patient setup at operation 504 may employ less rigid patient positioning techniques such as the patient laying on a couch or being seated in a chair that are frameless and/or maskless. Note that operation 504 can be implemented in any manner similar to that described and/or shown by the present disclosure, but is not limited to such.

At operation 506, an image (e.g., static or non-static) is loaded of at least one target volume of the patient. Note that operation 506 can be implemented in a wide variety of ways. For example, the image can be loaded at operation 506 by utilizing a cone beam computed tomography (CBCT) scan, an MRI scan, or any other medical imaging scan of the patient, but is not limited to such. Operation 506 can be implemented in any manner similar to that described and/or shown by the present disclosure, but is not limited to such.

At operation 508 of FIG. 5, based on the loaded image, the patient may be shifted or moved in order to align the patient to the ideal target orientation of a planning image used to simulate the patient's treatment. It is noted that operation 508 can be implemented in a wide variety of ways. For example, using the loaded image, the couch or chair that the patient is on or in can be 3D shifted at operation 508 in order to align the patient with the planning image (e.g., CT, MRI, or other medical imaging) used to simulate the patient's treatment, but is not limited to such. Note that operation 508 can be implemented in any manner similar to that described and/or shown by the present disclosure, but is not limited to such.

At operation 510, treatment of the patient begins with real-time fluoroscopic imaging. Note that operation 510 can be implemented in a wide variety of ways. For example, a four dimensional (4D) cone beam can be generated at operation 510 thereby resulting in a real-time video feed. It is noted that operation 510 can be implemented in any manner similar to that described and/or shown by the present disclosure, but is not limited to such.

At operation 512 of FIG. 5, a computation can be made (e.g., manually or automatically) as to whether the target volume of the real-time video imaging substantially aligns with the target volume of the planning image. If so, method 500 can proceed to operation 514. However, if at operation 512 it is computed that the target volume of the real-time video imaging does not substantially align with the target volume of the planning image, method 500 can proceed to the beginning of operation 512.

It is noted that operation 512 can be implemented in a wide variety of ways. For example, at operation 512, a manual monitoring can be implemented by a human (e.g., a therapist) that is trained to watch the real-time video imaging of the patient and determine when the target volume substantially aligns (e.g., within a range of deviation) with the intended target volume from the planning image (e.g., CT, MRI, or other medical imaging). In various embodiments, at operation 512, an automatic monitoring can be included using a computing system (e.g., 100) wherein one or more metrics are defined in order to compute when the target volume substantially aligns (e.g., within a range of deviation) with the intended target volume from the planning image (e.g., CT, MRI, or other medical imaging).

Figure 6:
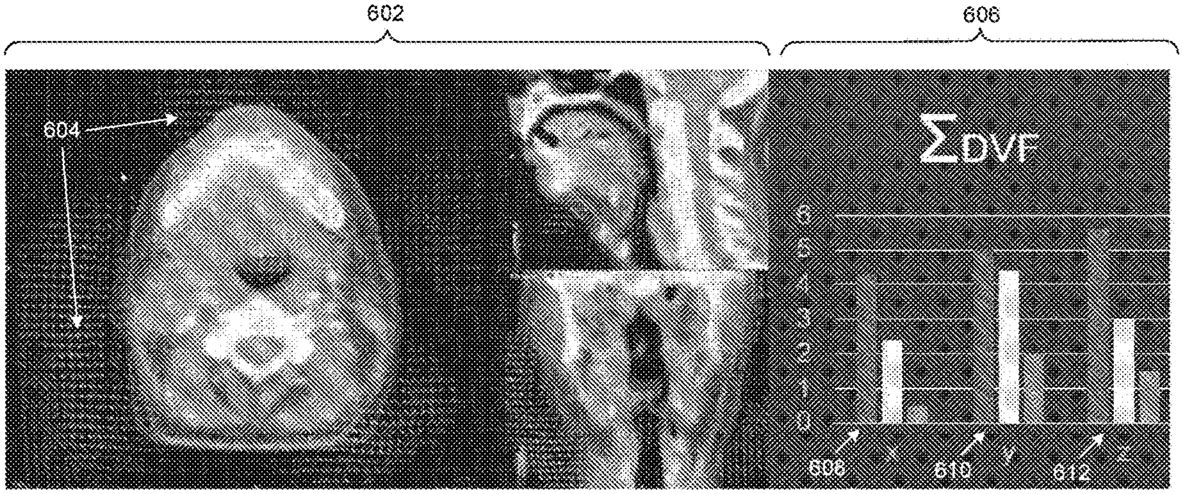
FIG. 6 illustrates a visual representation in accordance with various embodiments of the present disclosure.

In various embodiments, operation 512 of FIG. 5 can be implemented utilizing a visual representation of the mapping and alignment (e.g., within a range of deviation) of the real-time video imaging and the target volume of the planning image (e.g., CT, MRI, or other medical imaging). For example, FIG. 6 illustrates a visual representation 600 of the sum of a real-time deformation vector-field with colors in accordance with various embodiments of the present disclosure. More specifically, the visual representation 600 illustrates the sum of a real-time deformation vector-field with colors guiding a human user (e.g., therapist) to when the vector field magnitude is minimizing. Note that when the vector field magnitude is minimizing, the real-time video imaging of the target volume substantially aligns (e.g., within a range of deviation) with the target volume of the planning image.

It is noted that the visual representation 600 in various embodiments can include a deformation vector-field images 602 and a bar graph 606. The visual representation 600 can be generated by doing a deformable image registration where each voxel of the real-time video imaging will be mapped to a voxel in the planning image and that voxel mapping can be represented by deformation vector-fields 604 as shown in the vector-field images 602. It is pointed out that where there is a lot of change from one image to the other is represented by long arrows or vectors 604 and where there is not so much is represented by small arrows 604. Therefore, when the lengths of the arrows 604 get minimized within a region of interest (e.g., target volume), the treatment beam can be triggered (e.g., at operation 514). In addition, in various embodiments, the arrows 604 can be color coded where lighter colors indicate areas of higher deformation between the images while darker colors indicate areas of less deformation, but is not limited to such.

Within FIG. 6, in various embodiments, the bar graph 606 illustrates the summing of the deformation vector-field in each direction resulting in a quick activation of the magnitude of how long those arrows are in the x, y, and z directions. Within the bar graph 606, each of the x, y and z would include a bar 608, 610, or 612, respectively, indicating how close the first image is to being aligned with the second image (e.g., planning image). The shorter the bar, the closer the two images are aligned. Conversely, the longer the bar, the larger the two images are misaligned. In various embodiments, the bars can each be color coded. For example, a red bar represents misalignment between the two images, a yellow bar represents better alignment, and a green bar indicates an acceptable or desirable range of alignment between the two images. In various embodiments of the bar graph 606, it is noted that each of the x, y and z would include a single bar 608, 610, or 612, respectively, that can change in real-time.

Note that the visual representation 600 may not include all of the elements illustrated by FIG. 6. In addition, the visual representation 600 can be implemented to include one or more elements not illustrated by FIG. 6. It is pointed out that the visual representation 600 can be utilized or implemented in any manner similar to that described and/or shown by the present disclosure, but is not limited to such.

Within FIG. 5, operation 512 can be implemented utilizing a different visual representation than that shown within FIG. 6. For example, in various embodiments, a visual representation can enable the "drawing" of a three-dimensional volume around a target area or region of interest. Within that region of interest, the magnitude of the real-time deformation vector-field can be summed in real-time resulting in a metric (e.g., a number that is changing in real-time). When that number gets minimized (or within a defined range), a treatment beam can be triggered (e.g., at operation 514). Note that operation 512 can be implemented in any manner similar to that described and/or shown by the present disclosure, but is not limited to such.

At operation 514, a treatment is triggered which can include, but is not limited to, delivering a dose of radiation therapy (or ultrasound, etc.) to the target volume within a fraction of a second (e.g., less than a second). Note that operation 514 can be implemented in a wide variety of ways. For example, at operation 514, the entire treatment dosage of radiation therapy can be delivered to the target volume within a fraction of a second. In various embodiments, at operation 514, a fraction of the treatment dosage of radiation therapy can be delivered to the target volume within a fraction of a second. In various embodiments, at operation 514, each beam can deliver a relatively high dose in a relatively short period of time. For example, each beam can deliver, but is not limited to, at least 0.01 grays (Gy) or 4 Gy in less than one second, and may deliver as much as 20 Gy or 500 Gy or more in less than one second (sec). In various embodiments, at operation 514, each beam can deliver, but is not limited to, greater than 4 Gy/sec, greater than 20 Gy/sec, or greater than 40 Gy/sec. In various embodiments, at operation 514, each beam can deliver, but is not limited to, at least 1 Gy in 0.25 sec, at least 1 Gy in 0.05 sec, or at least 1 Gy in 0.025 sec. It is noted that operation 514 can be implemented in any manner similar to that described and/or shown by the present disclosure, but is not limited to such.

At operation 516 of FIG. 5, an online (or during treatment) triggered treatment quality assurance can be performed. It is noted that operation 516 can be implemented in a wide variety of ways. For example, by acquiring the fluoroscopy during treatment at operation 516, the 4D (four-dimensional) imaging information can be matched to the 4D beam-time, lending itself to a 4D dose calculation. In various embodiments, this calculation can be summed in real-time at operation 516 for online quality assurance (QA) while the next beam is being delivered, allowing for 4D dose tracking for each fraction in the course of treatment. Note that operation 516 can be implemented in any manner similar to that described and/or shown by the present disclosure, but is not limited to such.

At operation 518, a computation can be made as to whether the treatment has been completed. If so, method 500 can proceed to operation 522. However, if it is computed at operation 518 that the treatment has not been completed, method 500 can proceed to operation 520. Note that operation 518 can be implemented in a wide variety of ways. For example, operation 518 can be implemented in any manner similar to that described and/or shown by the present disclosure, but is not limited to such.

At operation 520 of FIG. 5, move to the next beam position or angle. It is noted that operation 520 can be implemented in a wide variety of ways. For example, moving to the next beam position or angle at operation 520 can be implemented by rotating a gantry (e.g., 420). In various embodiments, moving to the next beam position at operation 520 can be implemented by rotating the patient. Note that operation 520 can be implemented in any manner similar to that described and/or shown by the present disclosure, but is not limited to such. After operation 520 is completed, method 500 can proceed to the beginning of operation 510.

At operation 522, an offline (or after treatment) triggered treatment quality assurance can be performed. Note that operation 522 can be implemented in a wide variety of ways. For example, by acquiring the fluoroscopy after treatment at operation 522, the 4D imaging information can be matched to the 4D beam-time, lending itself to a 4D dose calculation. In various embodiments, this calculation can be summed for offline quality assurance (QA) at operation 522 allowing for 4D dose tracking for each fraction in the course of treatment. In various embodiments, at operation 522 the offline triggered treatment quality assurance can include checking, making sure, and redelivering (or replaying) the dose computationally on the 4D image with the actual log files from the machine and verify the dose that was done. It is pointed out that this utilization of fluoroscopy for 4D dose tracking may be useful for standard radiation delivery schemes and dose-rates. It is noted that operation 522 can be implemented in any manner similar to that described and/or shown by the present disclosure, but is not limited to such. After the completion of operation 522, method 500 can be ended. In this manner, method 500 can perform triggered radiation therapy treatment in accordance with various embodiments of the present disclosure.

Figure 7:
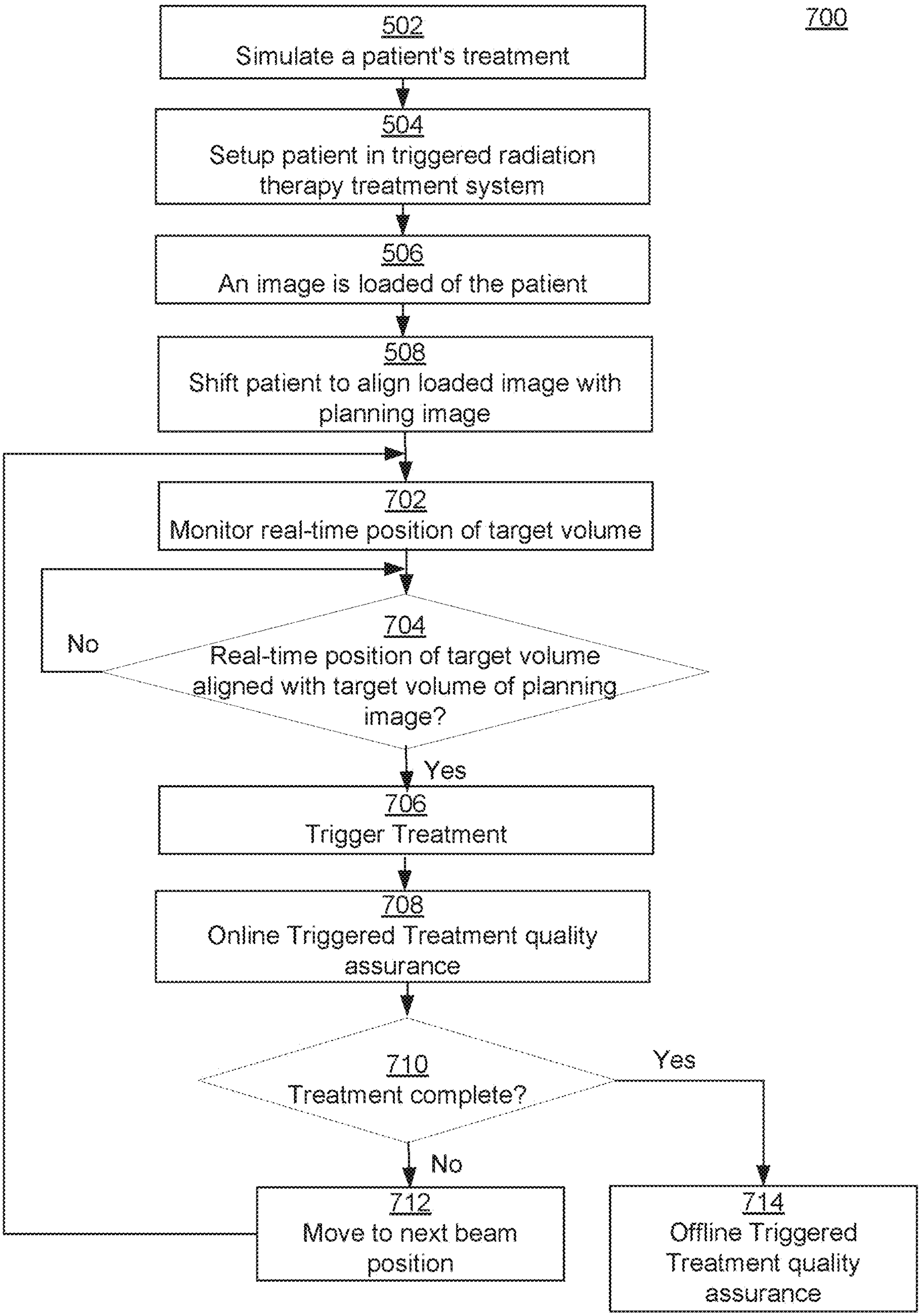
FIG. 7 is a flow diagram of a method in accordance with various embodiments of the present disclosure.

FIG. 7 is a flow diagram of a method 700 for performing triggered treatment (e.g., radiation therapy, ultrasound, etc.) in accordance with various embodiments of the present disclosure. Although specific operations are disclosed in FIG. 7, such operations are examples. The method 700 may not include all of the operations illustrated by FIG. 7. Also, method 700 may include various other operations and/or variations of the operations shown. Likewise, the sequence of the operations of flow diagram 700 can be modified. It is appreciated that not all of the operations in flow diagram 700 may be performed. In various embodiments, one or more of the operations of method 700 can be controlled or managed by software, by firmware, by hardware or by any combination thereof, but is not limited to such. Method 700 can include processes of various embodiments of the present disclosure which can be controlled or managed by a processor(s) and electrical components under the control of computer or computing device readable and executable instructions or code (e.g., the optimizer model 150 of FIG. 1). The computer or computing device readable and executable instructions (or code) may reside, for example, in data storage features such as computer or computing device usable volatile memory, computer or computing device usable non-volatile memory, and/or computer or computing device usable mass data storage. However, the computer or computing device readable and executable instructions (or code) may reside in any type of computer or computing device readable medium or memory (e.g., like those found within the computing system 100 of FIG. 1).

In various embodiments, note that the operations 502, 504, 506, and 508 of FIG. 7 can be performed similar to the operations 502, 504, 506, and 508 of FIG. 5 as described and/or shown by the present disclosure, but are not limited to such. It is noted that after the completion of operation 508 of FIG. 7, method 700 proceeds to operation 702 of FIG. 7.

At operation 702 of FIG. 7, treatment of the patient begins with monitoring (or continuously tracking) the real-time position of at least one target volume of the patient. Note that operation 702 can be implemented in a wide variety of ways. For example, monitoring (or continuously tracking) the real-time position of at least one target volume of the patient at operation 702 can be implemented with, but is not limited to, real-time fluoroscopic imaging, magnetic resonance imaging (MRI), fiducial markers, cone beam computed tomography (CBCT), digital tomosynthesis (DTS), ultrasound, external markers, any form of visualizing internal anatomy, surrogates of internal anatomy, 4D cone beam resulting in a real-time video feed, and the like. It is noted that operation 702 can be implemented in any manner similar to that described and/or shown by the present disclosure, but is not limited to such.

At operation 704, a computation can be made (e.g., manually or automatically) as to whether the real-time position of the at least one target volume substantially aligns with the position of the corresponding at least one target volume of the planning image. If so, method 700 can proceed to operation 706. However, if at operation 704 it is computed that the real-time position of the at least one target volume does not substantially align with the corresponding at least one target volume of the planning image, method 700 can proceed to the beginning of operation 704.

It is noted that operation 704 can be implemented in a wide variety of ways. For example, at operation 704, a manual monitoring can be implemented by a human (e.g., a therapist) that is trained to watch the real-time position of the at least one target volume and determine when it substantially aligns (e.g., within a range of deviation) with the corresponding at least one target volume from the planning image (e.g., CT, MRI, or other medical imaging). In various embodiments, at operation 704, an automatic monitoring can be included using a computing system (e.g., 100) wherein one or more metrics are defined in order to compute when the real-time position of the at least one target volume substantially aligns (e.g., within a range of deviation) with the corresponding at least one target volume from the planning image (e.g., CT, MRI, or other medical imaging).

In various embodiments, operation 704 of FIG. 7 can be implemented utilizing a visual representation of the mapping and alignment (e.g., within a range of deviation) of the real-time position of the at least one target volume and the corresponding at least one target volume from the planning image (e.g., CT, MRI, or other medical imaging) in any manner similar to that described and/or shown by the present disclosure, but is not limited to such. In various embodiments, it is noted that operation 704 of FIG. 7 can be implemented in any manner similar to operation 512 of FIG. 5 as described and/or shown by the present disclosure, but is not limited to such.

At operation 706, a treatment is triggered which can include, but is not limited to, delivering a dose of radiation therapy (or ultrasound, etc.) to the at least one target volume within a fraction of a second (e.g., less than a second). Note that operation 706 can be implemented in a wide variety of ways. For example, at operation 706, the entire treatment dosage of radiation therapy can be delivered to the at least one target volume within less than a second. In various embodiments, at operation 706, a fraction of the treatment dosage of radiation therapy can be delivered to the target volume within less than a second. In various embodiments, at operation 706, each beam can deliver a relatively high dose in a relatively short period of time. For example, each beam can deliver, but is not limited to, at least 0.01 Gy or 4 Gy in less than one second, and may deliver as much as 20 Gy or 500 Gy or more in less than one second (sec). In various embodiments, at operation 706, each beam can deliver, but is not limited to, greater than 4 Gy/sec, greater than 20 Gy/sec, or greater than 40 Gy/sec. In various embodiments, at operation 706, each beam can deliver, but is not limited to, at least 1 Gy in 0.25 sec, at least 1 Gy in 0.05 sec, or at least 1 Gy in 0.025 sec. It is noted that operation 706 can be implemented in any manner similar to that described and/or shown by the present disclosure, but is not limited to such.

At operation 708 of FIG. 7, an online (or during treatment) triggered treatment quality assurance can be performed. It is noted that operation 708 can be implemented in a wide variety of ways. For example, by acquiring the data (or information) of the real-time position monitoring of the at least one target volume during treatment at operation 708, it can be matched to the 4D beam-time, lending itself to a 4D dose calculation. In various embodiments, this calculation can be summed in real-time at operation 708 for online quality assurance (QA) while the next beam is being delivered, allowing for 4D dose tracking for each fraction in the course of treatment. Note that operation 708 can be implemented in any manner similar to that described and/or shown by the present disclosure, but is not limited to such.

At operation 710, a computation can be made as to whether the treatment has been completed. If so, method 700 can proceed to operation 714. However, if it is computed at operation 710 that the treatment has not been completed, method 700 can proceed to operation 712. Note that operation 710 can be implemented in a wide variety of ways. For example, operation 710 can be implemented in any manner similar to that described and/or shown by the present disclosure, but is not limited to such.

At operation 712 of FIG. 7, move to the next beam position or angle. It is noted that operation 712 can be implemented in a wide variety of ways. For example, moving to the next beam position or angle at operation 712 can be implemented by rotating a gantry (e.g., 420). In various embodiments, moving to the next beam position at operation 712 can be implemented by rotating the patient. Note that operation 712 can be implemented in any manner similar to that described and/or shown by the present disclosure, but is not limited to such. After operation 712 is completed, method 700 can proceed to the beginning of operation 702.

At operation 714, an offline (or after treatment) triggered treatment quality assurance can be performed. Note that operation 714 can be implemented in a wide variety of ways. For example, by acquiring the data (or information) of the real-time position monitoring of the at least one target volume after treatment at operation 714, it can be matched to the 4D beam-time, lending itself to a 4D dose calculation. In various embodiments, this calculation can be summed for offline quality assurance (QA) at operation 714 allowing for 4D dose tracking for each fraction in the course of treatment. In various embodiments, at operation 714 the offline triggered treatment quality assurance can include checking, making sure, and redelivering (or replaying) the dose computationally on a 4D image (for example) with the actual log files from the machine and verify the dose that was done. It is pointed out that in various embodiments, this utilization of fluoroscopy (or other position monitoring technique) for 4D dose tracking may be useful for standard radiation delivery schemes and dose-rates. It is noted that operation 714 can be implemented in any manner similar to that described and/or shown by the present disclosure, but is not limited to such. After the completion of operation 714, method 700 can be ended. In this manner, method 700 can perform triggered treatment (e.g., radiation therapy, ultrasound, etc.) in accordance with various embodiments of the present disclosure.

The foregoing descriptions of various specific embodiments in accordance with the present disclosure have been presented for purposes of illustration and description. They are not intended to be exhaustive or to limit the present disclosure to the precise forms disclosed, and many modifications and variations are possible in light of the above teaching. The present disclosure is to be construed according to the Claims and their equivalents.

What is claimed is:

1. A radiation therapy system comprising:
a memory storing instructions; and
a processor configured to execute the instructions to cause the radiation therapy system to,
obtain a planning image of a target in a human,
monitor a position of the target,
compute an occurrence of substantial alignment between the position of the target and the target of the planning image based on a real-time deformation vector-field within a region of interest, and
trigger a beam of radiation to deliver radiation therapy to the target in less than a second upon the occurrence of substantial alignment.

2. The radiation therapy system of claim 1, wherein the processor is configured to execute the instructions to cause the radiation therapy system to monitor the position of the target using a real-time video feed.

3. The radiation therapy system of claim 1, wherein the processor is configured to execute the instructions to cause the radiation therapy system to monitor the position of the target using real-time fluoroscopic imaging.

4. The radiation therapy system of claim 1, wherein the processor is configured to execute the instructions to cause the radiation therapy system to monitor the position of the target using magnetic resonance imaging.

5. The radiation therapy system of claim 1, wherein the processor is configured to execute the instructions to cause the radiation therapy system to monitor the position of the target using cone beam computed tomography.

6. The radiation therapy system of claim 1, wherein the processor is configured to execute the instructions to cause the radiation therapy system to monitor the position of the target using digital tomosynthesis.

7. The radiation therapy system of claim 1, wherein the processor is configured to execute the instructions to cause the radiation therapy system to monitor the position of the target using ultrasound.

8. The radiation therapy system of claim 1, wherein the processor is configured to execute the instructions to cause the radiation therapy system to monitor the position of the target using fiducial markers.

9. The radiation therapy system of claim 1, wherein the beam of radiation comprises at least one of protons, photons, ions, or electrons.

10. The radiation therapy system of claim 1, wherein the planning image comprises at least one of a magnetic resonance imaging image or a computed tomography image.

11. A radiation therapy system comprising:
a memory storing instructions; and
a processor configured to execute the instructions to cause the radiation therapy system to,
obtain a planning image of at least one target volume in a human,
continuously track a real-time position of the at least one target volume,
compute an occurrence of substantial alignment between the real-time position of the at least one target volume and the at least one target volume of the planning image based on a real-time deformation vector-field within a region of interest, and
trigger delivery of a dose of radiation therapy to the at least one target volume in less than a second upon the occurrence of substantial alignment.

12. The radiation therapy system of claim 11, wherein the processor is configured to execute the instructions to cause the radiation therapy system to continuously track the real-time position of the at least one target volume using real-time fluoroscopic imaging.

13. The radiation therapy system of claim 11, wherein the processor is configured to execute the instructions to cause the radiation therapy system to continuously track the real-time position of the at least one target volume using magnetic resonance imaging.

14. The radiation therapy system of claim 11, wherein the processor is configured to execute the instructions to cause the radiation therapy system to continuously track the real-time position of the at least one target volume using surrogates of internal anatomy.

15. The radiation therapy system of claim 11, wherein the processor is configured to execute the instructions to cause the radiation therapy system to continuously track the real-time position of the at least one target volume using cone beam computed tomography.

16. A radiation therapy system comprising:
a memory storing instructions; and
a processor configured to execute the instructions to cause the radiation therapy system to,
obtain a planning image of at least one target volume in a human,
continuously track a real-time position of the at least one target volume using four-dimensional (4D) cone beam computer tomography resulting in a real-time video feed,
compute an occurrence of substantial alignment between the real-time position of the at least one target volume and the at least one target volume of the planning image based on a real-time deformation vector-field within a region of interest, and
trigger delivery of a dose of radiation therapy to the at least one target volume in less than a second upon the occurrence of substantial alignment.

17. The radiation therapy system of claim 16, wherein the region of interest comprises a volume.

18. The radiation therapy system of claim 16, wherein the planning image comprises a magnetic resonance imaging image.

19. The radiation therapy system of claim 16, wherein the dose of radiation therapy comprises at least one of protons, photons, ions, or electrons.

20. The radiation therapy system of claim 16, wherein the planning image comprises a computed tomography image.

* * * * *